US006752994B2

(12) United States Patent
Jacobs, Jr. et al.

(10) Patent No.: US 6,752,994 B2
(45) Date of Patent: *Jun. 22, 2004

(54) INSERTIONAL MUTATIONS IN MYCOBACTERIA

(75) Inventors: William R. Jacobs, Jr., City Island, NY (US); Barry Bloom, Hastings-on-Hudson, NY (US); Ganjam V. Kalpana, Yonkers, NY (US); Jeffrey D. Cirillo, Mountain View, CA (US); Ruth McAdam, Near Hatfield (GB)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/898,762

(22) Filed: Jul. 3, 2001

(65) Prior Publication Data

US 2003/0100100 A1 May 29, 2003

Related U.S. Application Data

(63) Continuation of application No. 08/850,977, filed on May 5, 1997, now Pat. No. 6,566,121, which is a continuation of application No. 08/247,711, filed on May 23, 1994, now abandoned, which is a continuation-in-part of application No. 08/190,240, filed on Feb. 1, 1994, now abandoned, which is a continuation of application No. 07/806,706, filed on Dec. 12, 1991, now abandoned, which is a continuation-in-part of application No. 07/714,656, filed on Jun. 13, 1991, now abandoned.

(51) Int. Cl.[7] .................... A61K 39/04; A01N 63/00; C12N 1/00; C12N 1/12
(52) U.S. Cl. .................. 424/248.1; 424/93.1; 424/93.2; 435/243; 435/252.1; 435/253.1; 435/254.11; 435/440; 435/863; 435/864; 435/865; 435/866
(58) Field of Search ............................ 424/248.1, 93.1, 424/93.2; 435/252.1, 253.1, 254.11, 863, 864, 865, 866, 440, 243

(56) References Cited

U.S. PATENT DOCUMENTS

| | | |
|---|---|---|
| 5,504,005 A | 4/1996 | Bloom et al. |
| 5,672,345 A | 9/1997 | Curtiss, III |

FOREIGN PATENT DOCUMENTS

| | | |
|---|---|---|
| EP | 0166410 | 1/1986 |
| WO | WO 8806626 | 9/1988 |
| WO | 9000594 WO | 1/1990 |
| WO | 9010701 WO | 9/1990 |
| WO | 9015873 WO | 12/1990 |
| WO | WO 9201783 | 2/1992 |
| WO | WO 9201796 | 2/1992 |
| WO | WO 9221374 | 12/1992 |
| WO | WO 9222326 | 12/1992 |

OTHER PUBLICATIONS

Martin et al., entitled "Transposition of an Antibiotic Resistance Element in mycobacteria", Nature 345: 739–743, 1990.

Snapper et al., entitled "Isolation and characterization of efficient plasmid transformation mutants of *Mycobacterium smegmatis*", Mol. Microbiology 4; 1911–1919, 1990.
Snapper et al., Dissertation International 52/05–B p. 2415, 1990, Abstract Only.
Ranes et al., entitled "Functional analysis of pAL5000, a plasmid from *Mycobacterium fortuitum*:construction of a "mini" mycobacterium–*Escherichia coli* shuttle vector", Journal of Bacteriology 172; 2793–2797, 1990.
Cirillo et al., Abstracts of the Annual Meeting of the American Society for Microbiology, May 13–17, p. 143, Abstract No. U–13, 1990.
Subramanyam et al., entitled Partial characterization of *Mycobacterium fortuitum* and *Mycobacterium smegmatis* auxotrophs by syntrophism using *Bacillus subtilis*, Journal of General Microbiology 135; 2651–2654.
Subramanyam et al., Letters in Applied Microbiology 8; 161–164–1989.
Woodley et al., entitled "Isolating specific auxotrophic mutants of *Mycobacterium smegmatis* by using vancomycin", Antimicrob Agents Chemother 19; 571–574, 1981.
Cirillo, et al., A Novel Transposon Trap for Mycobacteria: Isolation and Characterization of IS1096, Journal of Bacteriology, Dec. 1991, vol. 173, No. 24, pp. 7772–7780.
Jacobs, Jr., et al., Genetic Systems for Mycobacteria, Methods in Enzymology, vol. 204, pp. 537–555, 1991.
Thole, et al., Characterization, sequence determination and immunogenicity of a 64–Kilodalton protein of mycobacterium bovis BCG expressed in *E. Coli* K–12, 55(6) Infection and Immunity, pp. 1466–1475, 1987.
Jacobs, et al., Development of BCG as a Recombinant Vaccine Vehicle, Curr. Topics in Microbiology & Immunology, 155, pp. 153–160 (1990).
Kalpana, et al., Insertional Mutagenesis and Illegitimate Recombination in Mycobacteria, Proc. Natl. Acad. Sci., 88, pp. 5433–5437, Jun. 1991.
Ingraham, et al., eds., *Eschericia Coli* and *Salmonella Typhimurium*—Cellular and Molecular Biology, vol. 1, American Society for Microbiology, pp. x and xi, 1987.
Lugosi, et al., Genetic Transformation of BCG, Tubercle, 70, pp. 159–170 (1989).
Hayes, The Genetics of Bacteria and Their Viruses, 2d Ed., John Wiley & Sons, pp. 120–124 (1968).
England, et al., IS900—Promoted Stable Integration of a Foreign Gene into Mycobacteria, Molecular Microbiology, 5(8), pp. 2047–2052, 1991.

*Primary Examiner*—Rodney P Swartz
(74) *Attorney, Agent, or Firm*—Amster, Rothstein & Ebenstein LLP

(57) ABSTRACT

A mutated mycobacterium selected from the class consisting of mutated *M. bovis*-BCG, mutated *M. tuberculosis*, and mutated *M. leprae*. The mutation of *M. bovis*-BCG, *M. tuberculosis*, or *M. leprae* is preferably effected through an insertional mutation of a mycobacterial gene. The insertional mutagenesis may be effected, for example, through illegitimate recombination or by a mycobacterial transposon. Such mutated mycobacteria may then be transformed with an expression vector(s) containing a complement gene to the gene which is mutated, and preferably also including a heterologous gene.

12 Claims, 29 Drawing Sheets

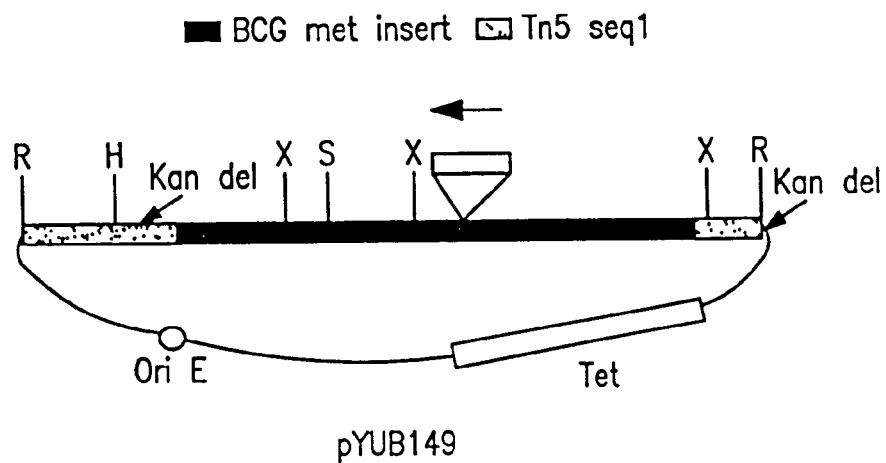
FIG. 8 pYUB149
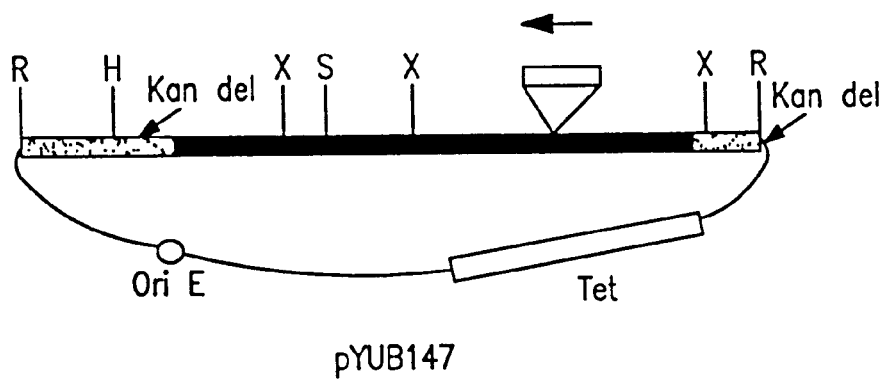
FIG. 9 pYUB147
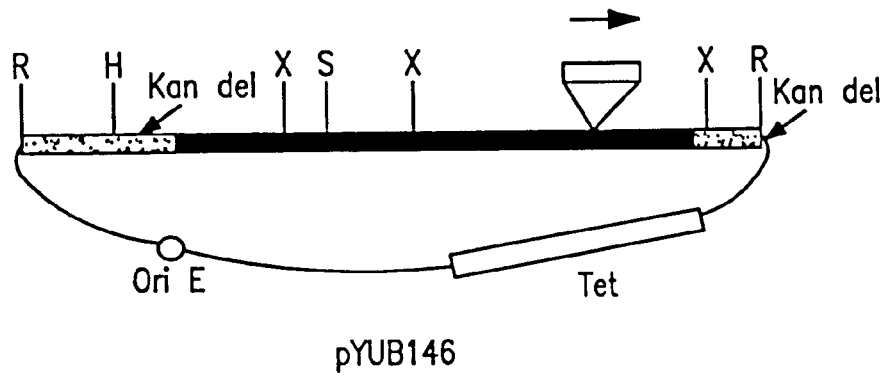
FIG. 10 pYUB146

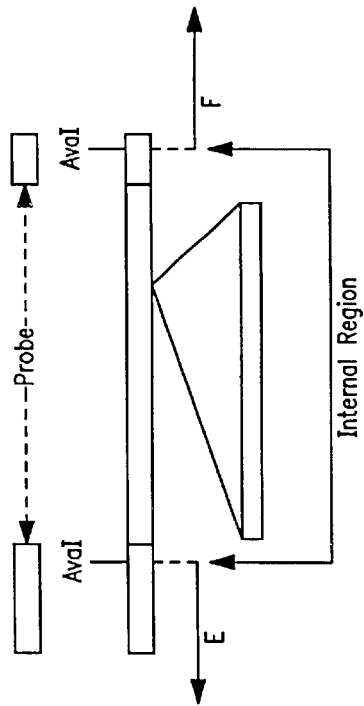
FIG. 11
FIG. 12
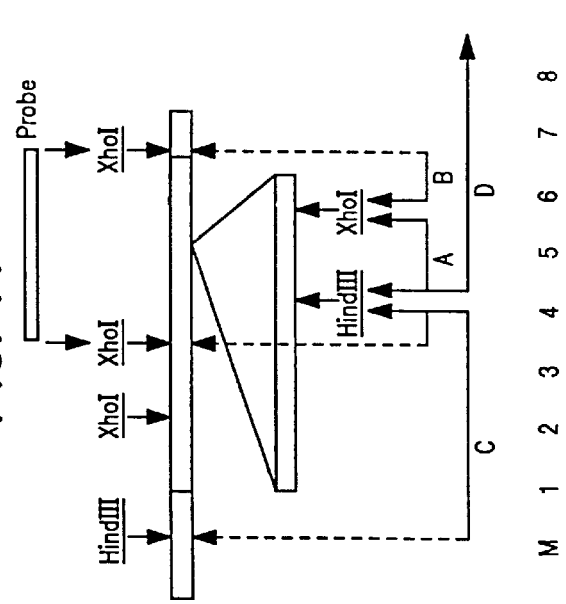

```
                      GGTTTCTGGCTCTCTTCGCACTTGACGGTGTAGAGACGATCAGCTGCTTTCGCGCTGTGATCGAGGGGTCTGGTTGGCT
                                             50                                    150
TGGGGTGTGCCGGAGAAGAAGCGGAAGAGCAAGAGCGGAGTGTCCGGGGCAGTGTGGACCTGGCGTTGCTGCAGAAGCT
 ↑        V  P  E  K  K  R  K  S  K  R  K  S  G  V  S  G  G  S  V  D  L  A  L  L  Q  K  L
 tnpR                                     200                                       250
AATGGCCGACGCTGGTCGGAGAAATGTTCGCGGGAATGTTCGATGAGCCGACTCCGGAGGTGCGGGTGCCCGATCGTGCCGGGG
 M  A  D  A  G  R  N  V  F  A  G  M  F  D  E  P  T  P  E  V  R  A  V  P  D  R  A  R
                                          300
GCTTCCGGGTCGCCGTCGACCTGATGTACGCCAAGCCGCCGATCTGGCGTCGGCTCGACCTGCCGGGCGACCTCATGCTCGATGAG
 G  F  R  V  R  V  D  L  M  Y  A  K  P  P  I  W  R  R  L  D  L  P  G  D  L  M  L  D  E
                         350                                                    400
CTCCATGTGTGCTCAGTCGTTATGGGCTGGCAGGACAGTCATCTGCATAAGTTCGGTGTCGGGGCGGACCGGCGGACCCGTGC
 L  H  V  L  Q  V  V  M  G  W  Q  D  S  H  L  H  K  F  G  V  G  A  D  R  R  T  R  A
                                   450                                               500
CTACTTCGTCACCGGGTTTGATCTCAGCGAAGGCGACAGCGTCGTCCTCGAGGACAGCGTGCGCCTCGATCAGTGGTGTCCGATA
 Y  F  V  T  G  F  D  L  S  E  G  D  D  G  V  V  E  D  S  V  R  L  D  Q  V  V  S  D
                    550
AGGGCGAGCGGTGTTCTACGATTACGACTTCGGCGATGGACCACGTGCTCGTGGTCGAAGACGTTTTCGATGATCCGCCC
 K  G  E  R  L  F  Y  D  Y  D  F  G  D  G  W  D  H  V  L  V  V  E  D  V  F  D  D  P  P
                 600                                                        650
CCGGCTGCGGTGTGTCTGACGGGAAAGATGGCCTGTCCCCGGAGGACTGTGGTGGCCGGCTATGAGGAGTTGGCTGCGTG
 P  A  A  V  C  L  T  G  K  M  A  C  P  P  E  D  C  G  G  L  G  G  Y  E  E  L  A  A  W
                            700                                                750
GGTTCGGGGGTACGAGGATCCGCCGGAAACCGGGATGGGACTCGGTGCGCCCCAGGAGATGAGGGACTGGCTGCCCGGGCTGGCAC
 V  R  G  G  Y  D  P  P  R  E  T  P  M  G  L  G  A  Q  E  M  R  D  W  L  P  P  G  L  A
                                     800                                               850
CCCGACACCGTTCTCGGTGGCCGAGACCAATGACGCTCTGGCCGTTGAACACGCCGTTGAGGATTCTTCACCGCCAGGTTGACGG
 P  R  P  F  L  G  G  R  D  Q  *                            *  R  R  P  Q  R
                                                                        BamHI
AGCTGGGTTCGAAGCCTCCGGTTCTCGAGCAGGAGCCGATGTAGTTGGTGAGTTGCGGAAGCCCAGGCGGATCCGGCCAG
 L  Q  T  R  F  G  G  T  E  L  L  S  R  A  I  Y  N  T  L  N  R  F  G  L  A  S  G  R  L
                                    900

FIG. 29A
```

```
                                                1000
GTGTTCGAGGCGGCCGTTGATCGCTTCGGTCCCGTTGGAGGTGCCGGGCGTCGAAGTAGCCAGGACGTCGGCGCACGCT
 H  E  L  R  G  N  I  A  E  T  P  G  N  S  T  G  P  R  D  F  Y  A  L  V  D  A  A  R  K
              1050                                                   1100
TCTTCAGTGTCCGCCCCGAGGGTGATCAGCTCCGGTCAGCGACGTGGGGACGCCCTGTGCTCAGCGTGTGATCAGCCATCATG
 K  L  T  R  G  L  T  I  L  E  T  L  S  T  P  V  G  T  S  L  T  T  I  L  A  A  M  M
                          1150
GTGCGGCCCTTGGTTCTCTGGTTCCGGTAGGCGCGTGCGTTGATACATCGCCCAGGTGGCCTCGATCTCGGCGTGCGC
 T  R  G  K  T  R  D  P  E  R  Y  A  A  V  T  R  Q  Y  M  A  W  T  A  E  I  E  A  H  A
 1200                                       1250
GTTGGCGGCGAACAGTGCGGGCCTTTCTGCGGTCGGTGAGCAGTGCCCCGGTGTGCAGGGTGCGCGTCGCGATCGGT
 N  A  A  F  L  A  A  L  R  A  K  Q  R  D  T  L  L  D  A  G  T  H  L  T  R  R  S  R  Y
                   1300                                             1350
AGAGCGGGTCGGTGCGCCCGCCAGTCGGCCGTCGGCCACTCGTCGGAGGGCGTTGCCGGCCAGG
 L  P  D  T  S  R  G  R  H  G  C  T  A  L  Q  V  R  R  C  E  D  L  A  N  G  A  L
                       1400   BstXI                                 1450
CGGACCACGTCGAAGGGTCCATCACCGTGGCCACCGATCCGCTCAGGCAGTTCTTCGGTGCCGGTCTTGAACCCGTCCAT
 R  V  V  H  F  P  D  M  V  T  A  A  D  P  L  E  E  T  A  A  T  K  F  G  S  F  G  D  M
                                BstXI        1500
GGCAACAAGTCCACAGCGATCACGCCAGTCCTGTGCCAGTCGGCAACGCCTTCTTGGAGCGGCCCTCCACCA
 A  V  D  V  R  D  R  W  E  Q  P  R  Q  A  L  W  D  A  F  A  K  K  S  R  G  E  V  M
                                           1600
TGTCGAGCAGCCGTGCGGCCGGTCGTGACGGTGGGAATGATGAGATCGATGATCATTGTGTACTTGTGCCGGCGAGTG
 D  L  L  R  A  P  G  T  G  D  R  V  P  T  L  D  I  I  V  T  V  Y  K  D  G  R  R  T
                       1650                                1700
TGCCGCCACACTGCTCATCGACGCGGATCACCGGACGGGCCCGATCGAACGGCGATGAGCACCCGCTGACCTTCGGC
 D  L  L  R  A  P  G  T  G  D  R  V  P  T  L  D  I  I  V  T  V  Y  K  D  G  R  R  T
                                  1750                                 1800
GAGCACGGCGTTGTTGGCAGTGTTCCACGACACCCAAGCGCTCGGCGACCAGGTGTTGGCAGACAAGGGCTT
 L  V  A  N  N  A  T  N  W  S  V  A  L  A  E  A  V  R  A  V  S  L  H  Q  C  V  L  A  E
                                       1850
CCAGGCCCACCGAGAGCACGCCGGACAGCCTGGGCGTTCGGCTGCATCCTGGCGCGGGCATGAGCGCAG
 L  A  W  R  L  A  R  R  S  L  R  A  R  P  E  A  A  A  S  A  D  Q  R  W  V  H  A  C

FIG. 29B
```

```
                                            1950
CCGGCGCAACGGTAACGGCGGATCGTGACCAGCAAAGCCGTGGGTCGCCACCCGAACGGTTCATGAGCCAACGTGCGAGTCACGCT
 G  A  C  R  Y  R  R  I  T  V  L  L  A  T  P  R  W  G  F  P  E  H  A  L  T  R  T  V  S
                2000                                                          2050
GTCACGTACAACGGCCTTCTTCGCCGGGGCGCACCAGCGATCCTCATCGGCGACCCGCCAGCACGGCCCGATCAGGGT
 D  R  V  V  G  E  E  G  C  R  R  C  W  R  D  E  D  A  V  R  C  A  L  V  A  R  D  P  D
                                    2100
CGAGGCGGTTGGCGGGTCACCTCCAACCCGAGCTCGTCGAGGGCAGAAAGTCGTCAGGCGAAGCCCGCACCGACC
 L  R  Q  G  T  V                                                     ← tnpA
         2150                                                  2200
GGTAGCCGTCAGGCACGTCGAGGTCTTTCAGATGGATGGCGTAGGAACCTCCATCATCGGAAGACCTCGACCCCCTATCCCGGCACCG
                                                          2250
ACGCGCCGACGACCTCTACACCCCTCAACTGCGAAGAGCCGGTTTCT
```

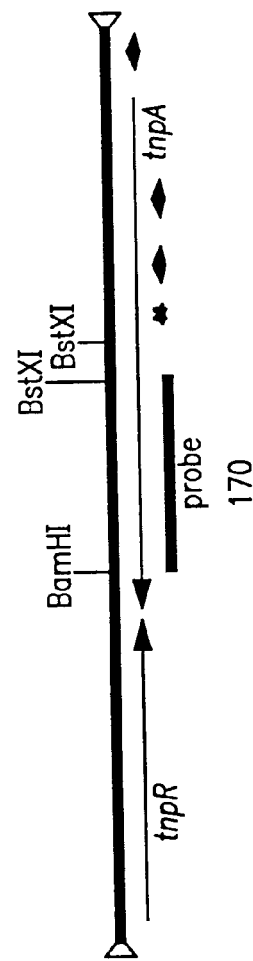

FIG. 29C

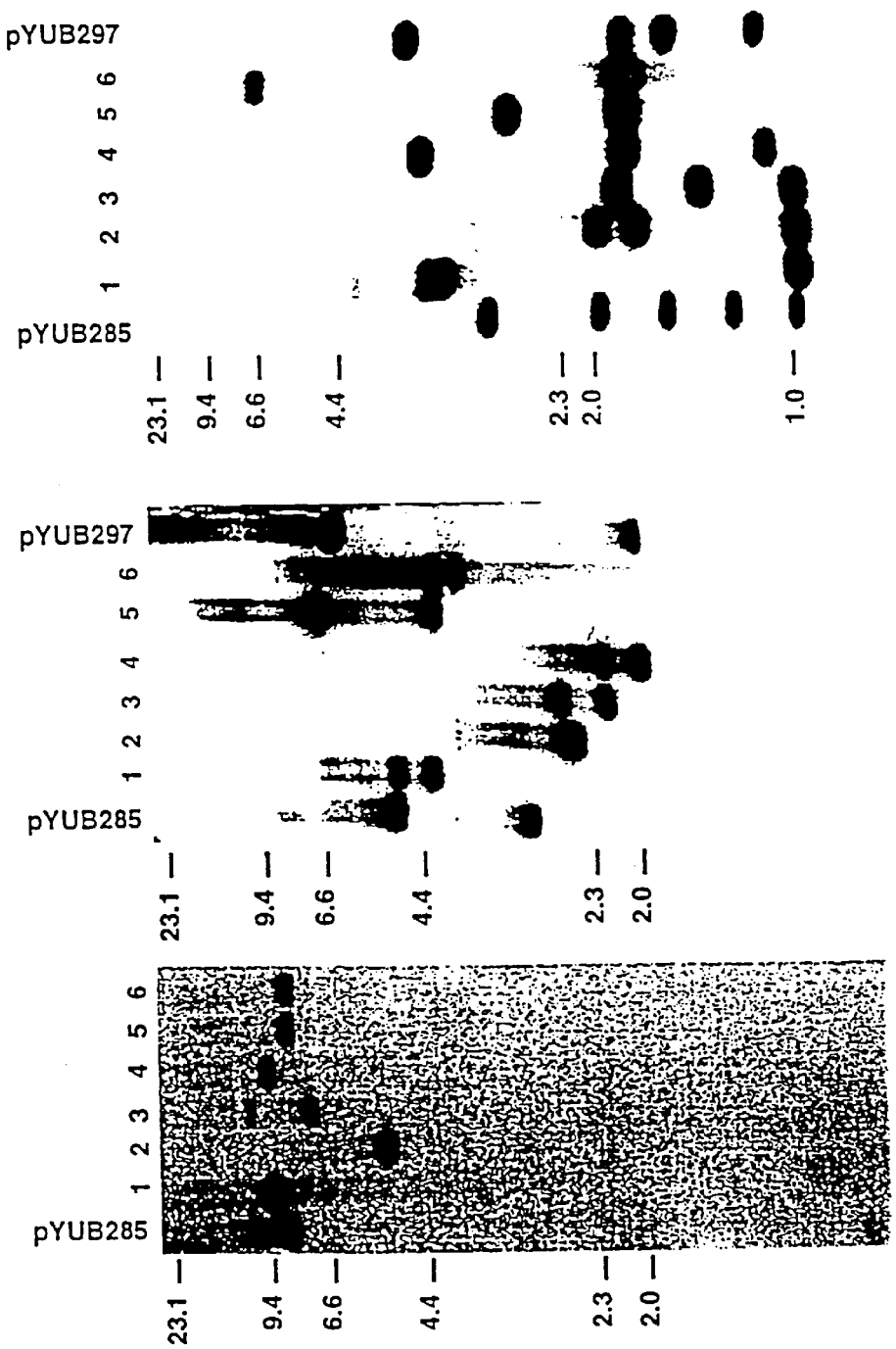

INSERTIONAL MUTATIONS IN MYCOBACTERIA

This application is a continuation of U.S. application Ser. No. 08/850,977, filed May 5, 1997, now U.S. Pat. No. 6,566,121 B1, issued May 20, 2003, which is a continuation of U.S. application Ser. No. 08/247,711, filed May 23, 1994, now abandoned, which is a continuation-in-part of application Ser. No. 08/190,240, filed Feb. 1, 1994, now abandoned, which is a continuation of application Ser. No. 07/806,706, filed Dec. 12, 1991, now abandoned, which is a continuation-in-part of application Ser. No. 07/714,656, filed Jun. 13, 1991, now abandoned.

This invention relates to mutagenesis of mycobacteria. More particularly, this invention relates to the generation of insertional mutations in mycobacteria.

Certain mycobacteria represent major pathogens of man and animals. For example, tuberculosis is generally caused in humans by *Mycobacterium tuberculosis*, and in cattle by *Mycobacterium bovis*, which may also be transmitted to humans and other animals. *Mycobacteria leprae* is the causative agent of leprosy. *M. tuberculosis* and mycobacteria of the avium-intracellulare-scrofulaceum group (MAIS group) represent major opportunistic pathogens of patients with acquired immune deficiency syndrome (AIDS). *M. pseudotuberculosis* is a major pathogen of cattle.

On the other hand, Bacille Calmette-Guerin, or BCG, an avirulent strain of *M. bovis*, is widely used in human vaccines, and in particular is used as a live vaccine, which is protective against tuberculosis. BCG is the only childhood vaccine which is currently given at birth, has a very low incidence of adverse effects, and can be used repeatedly in an individual (e.g., in multiple forms). In addition, BCG and other mycobacteria (e.g., *M. smegmatis*), employed in vaccines, have adjuvant properties among the best currently known and, therefore, stimulate a recipient's immune system to respond to antigens with great effectiveness.

It has been suggested by Jacobs, et al, *Nature, Vol.* 327, No. 6122, pgs. 532–535 (Jun. 11, 1987) that BCG could be used as a host for the construction of recombinant vaccines. In other words, it was suggested to take an existing vaccine (in this case against tuberculosis) and expand its protective repertoire through the introduction of one or more genes from other pathogens. Because BCG vaccines are administered as live bacteria, it is essential that any foreign antigens, polypeptides, or proteins expressed by the bacteria are not lost from the bacteria subsequent to vaccination.

Transformation, the process whereby naked DNA is introduced into bacterial cells, has been carried out successfully in mycobacteria. Jacobs, et al (1987), hereinabove cited, have described transformation of mycobacteria through chemical methods, and Snapper, et al. *PNAS, Vol.* 85, pgs. 6987–6991 (September 1988) have described transformation of mycobacteria by electroporation. Electroporation can give from $10^5$ to $10^6$ transformants per $\mu$g of plasmid DNA and such plasmid DNA's may carry genes for resistance to antibiotic markers such as kanamycin (Snapper, et al 1988) to allow for selection of transformed cells from non-transformed cells.

Jacobs, et al (1987) and Snapper, et al (1988) have also described the use of cloning vehicles, such as plasmids and bacteriophages, for carrying genes of interest into mycobacteria.

Combination of the above-mentioned techniques, along with standard tools of molecular cloning (e.g., use of restriction enzymes, etc.) allows the cloning of genes of interest into vectors and introduction of such genes into mycobacteria. To express these genes, it is important to have available signals for gene expression, in particular, transcription promoter elements. Such promoter elements have been isolated from mycobacterial heat shock genes, and have been used to express foreign antigens in mycobacteria.

Molecular genetics of mycobacteria, however has only recently begun to be developed, in part because mycobacteria present formidable obstacles to genetic study in that mycobacteria, in general, clump in culture and grow very slowly. The direct selection of mutants by employing transposons (also known as random insertional mutagenesis) has been a useful approach to the mutational analysis of microbial pathogenesis (Isberg, et al., *Curr. Top. Microbiol. Immunol.*, Vol. 118, pgs. 1–11 (1985); Taylor, et al., *J. Bacteriol,* Vol. 171, pgs. 1870–1878 (1989); Fields, et al., *Science,* Vol. 243, pgs. 1059–1061 (1989); Bernardini, et al., *Proc. Nat. Acad. Sci.*, Vol. 86, pgs. 3867–3871 (1989)); such selection of mutants, however, had not been described in mycobacteria.

Objects of the present invention include the generation of mutations in mycobacteria and/or the introduction of heterologous genes into mycobacteria; in particular, the generation of mutations of mycobacteria employed in vaccines, such as BCG, as well as the generation of mutations in pathogenic mycobacteria, such as *M. tuberculosis* or *M. leprae*, whereby such mutations make the mycobacteria non-pathogenic. Heterologous genes which may be introduced into the mycobacteria include, but are not limited to, genes for protective antigen(s) for a variety of pathogens, and/or for other therapeutic agents.

BRIEF DESCRIPTION OF THE DRAWINGS

FIG. 4. Representation of plasmid pYUB121-24a.

FIG. 8. Representation of plasmid pYUB149.

FIG. 9. Representation of plasmid pYUB147.

FIG. 10. Representation of plasmid pYUB146.

FIG. 11. Southern blot analysis of DNA from BCG methionine auxotroph (BCG strain mc$^2$576) and from two other kanamycin-resistant transformants using 1.8 kb XhoI DNA fragment from the BCG met gene as a probe. Analysis described in Example 3.

FIG. 12. Southern blot analysis of Hind III digested and XhoI digested chromosomal BCG DNA from nine additional kanamycin-resistant transformants, obtained by the transformation of linearized pYUB146, with the XhoI probe obtained from BCG met gene. Analysis described in Example 3.

FIGS. 29A–29C. Nucleotide and amino acid sequences of IS1096. C: Representation of internal IS1096 fragment shown as a solid bar between BamHI and BstXI sites. Described in Example 7.

FIGS. 32A–32C. Southern blot analysis of strains mc²826—mc²831 using plasmid pYUB285 as a probe and enzymes KpnI (FIG. 32A), BamHI (FIG. 32B), and PvuI (FIG. 32C).

Figure 1:
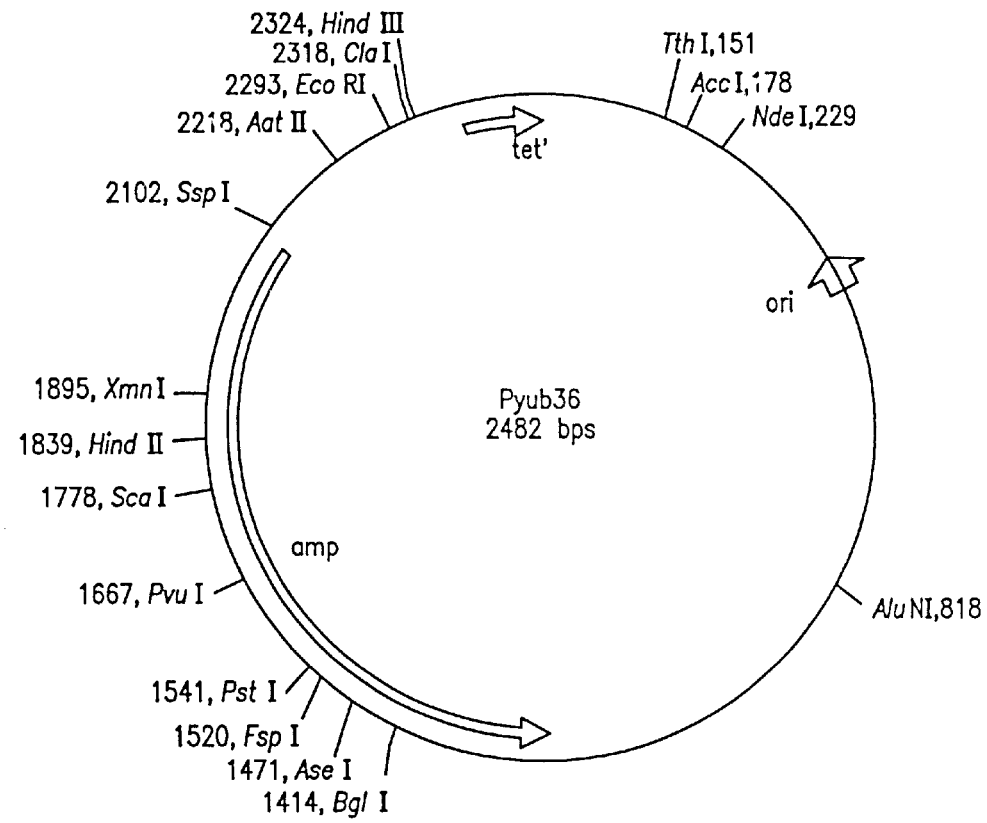
FIG. 1. Representation of plasmid Pyub36. Pyub36 contains a gene (amp) for ampicillin resistance.

In accordance with an aspect of the present invention, there is provided a mutated mycobacterium selected from the class consisting of mutated *M. bovis*-BCG, mutated *M. tuberculosis*, and mutated *M. leprae*. The term "mutated *M. bovis*-BCG", or "mutated BCG", or "mutated *M. tuberculosis*", or "mutated *M. leprae*" as used herein means that the *M. bovis*-BCG, *M. tuberculosis*, or *M. leprae* includes at least one mutated gene such that the expression or the function of the gene is varied with respect to the non-mutated gene in the parent strain.

Preferably, the mycobacterium is mutated through an insertional mutation of a mycobacterial gene. The insertional mutation of the mycobacterial gene may be effected through illegitimate recombination of DNA into the mycobacterial chromosome, or by homologous recombination, or by the insertion of a mycobacterial transposon into a mycobacterial gene, or by the transfection of a mycobacterium with a vector which includes a pair of inverted repeat sequences and DNA encoding a transposase. Preferably the insertional mutation is effected by illegitimate recombination of DNA into the mycobacterial chromosome.

In accordance with another aspect of the present invention, there is provided a mutated *M. bovis* which is mutated through an insertional mutation of an *M. bovis* gene. The insertional mutation of the *M. bovis* gene may be effected as hereinabove described for mutated *M. bovis*-BCG, mutated *M. tuberculosis*, and mutated *M. leprae*.

The DNA which is integrated into the mycobacterial chromosome through illegitimate recombination may be a linear DNA fragment or may be a circular DNA. Preferably, the DNA is a linear DNA fragment.

Applicants have found that illegitimate recombination, which is a rare phenomenon in prokaryotes, may be effected in *M. bovis*-BCG and *M. tuberculosis* by transforming BCG or *M. tuberculosis* with a linearized plasmid. Transformation may be accomplished by any means known to those skilled in the art, such as, for example, electroporation, or by the generation of protoplasts into which the transforming DNA is inserted, followed by regeneration of the cell wall, as described in Jacobs (1987) and Snapper (1988).

In one embodiment, the DNA which is integrated into the mycobacterium chromosome through illegitimate recombination includes a selectable marker. Selectable markers which may be employed included a kanamycin resistance marker, a bleomycin resistance marker, or a hygromycin resistance marker, or a bacteriophage resistance marker, such as, but not limited to, mycobacteriophage L5, L1, Bxb1, Bxb2, Bxb3, D29, or TM4 resistance markers.

In another embodiment, the DNA includes at least one DNA sequence which encodes a protein heterologous to mycobacteria.

The at least one DNA sequence which encodes a protein heterologous to mycobacteria may be DNA which is all or a portion of a gene encoding protein(s) or polypeptide(s) of interest.

Proteins or polypeptides of interest, which may be encoded by the at least one DNA sequence include, but are not limited to, antigens, anti-tumor agents, enzymes, lymphokines, pharmacologic agents, immunopotentiators, and reporter molecules of interest in a diagnostic context.

Antigens for which the at least one DNA sequence may encode include, but are not limited to, *Mycobacterium leprae* antigens; *Mycobacterium tuberculosis* antigens; Rickettsia antigens; malaria sporozoites and merozoites; diphtheria toxoids; tetanus toxoids; Clostridium antigens; Leishmania antigens; Salmonella antigens; Borrelia antigens; *Mycobacterium africanum* antigens; *Mycobacterium intracellulare* antigens; *Mycobacterium avium* antigens; Treponema antigens; Pertussis antigens; Schistosoma antigens; Filaria antigens; Herpes virus antigens; influenza and parainfluenza virus antigens; measles virus antigens; mumps virus antigens; hepatitis virus antigens; Shigella antigens; Neisseria antigens; rabies antigens, polio virus antigens; Rift Valley Fever virus antigens; dengue virus antigens; Human Immunodeficiency Virus (HIV) antigens; respiratory syncytial virus (RSV) antigens; snake venom antigens; and *Vibrio cholera* antigens. Enzymes which may be encoded include, but are not limited to, steroid enzymes.

Anti-tumor agents which may be encoded by the at least one DNA sequence include, but are not limited to, interferon-α, interferon-β, or interferon-γ, and tumor necrosis factor, or TNF. Lymphokines which may be encoded include, but are not limited to, interleukins 1 through 8.

Reporter molecules which may be encoded include, but are not limited to, luciferase, B-galactosidase, B-glucuronidase, and catechol dehydrogenase.

Other peptides or proteins which may be encoded by the at least one DNA sequence include, but are not limited to, those which encode for stress proteins, which can be administered to evoke an immune response or to induce tolerance in an autoimmune disease (e.g., rheumatoid arthritis).

In one embodiment the DNA which integrates into the mycobacterial chromosome through illegitimate recombination may be derived from a plasmid. The plasmid may be a shuttle plasmid which includes a bacterial origin of replication such as an *E. coli* origin of replication, a Bacillus origin of replication, a Staphylococcus origin of replication, a Streptomyces origin of replication, or a pneumococcal origin of replication. The plasmid, in another embodiment, may include a mycobacterial origin of replication, or may be a shuttle plasmid including a mycobacterial origin of replication plus a bacterial origin of replication as hereinabove described. Preferably, the plasmid is linearized prior to integration into the mycobacterial chromosome through illegitimate recombination.

In a preferred embodiment, a linear DNA, such as, for example, a linearized plasmid, is integrated into an *M. bovis* chromosome, an *M. bovis*-BCG chromosome or an *M. tuberculosis* chromosome, or an *M. leprae* chromosome, such as, for example, a BCG chromosome, through illegitimate recombination. The DNA, through such integration, will cause an insertional mutation of a gene(s) in the mycobacterial chromosome. For example the DNA may cause an insertional mutation of a gene encoding an enzyme which is essential in a biosynthetic pathway of a nutrient or an amino acid. The transformed mycobacteria are then screened in order to determine the gene(s) which is mutated. For example, the mutated mycobacteria may be grown on minimal media (without amino acids) and on media containing various amino acids to determine the nutritional requirements of the mutated mycobacteria; i.e., the mutated mycobacteria may be screened for auxotrophy. Once the mutated gene is identified, the complement (i.e., non-mutated) gene is isolated and cloned into an expression vector. The expression vector is then transformed into the mutated mycobacterium, whereby the complement gene is expressed in the mutated mycobacterium, and the mutated mycobacterium becomes prototrophic. The expression vector may also include a gene encoding for protein or polypeptide heterologous to the mutated mycobacterium. Such proteins or polypeptides may be those which are hereinabove described. Selection for mutated mycobacteria containing the complement gene and a gene encoding for a heterologous protein or polypeptide may thus be based on the ability of the mutated mycobacteria, into which the complement and the heterologous genes are introduced, to survive, when such mutated mycobacteria are grown on appropriate media.

In one embodiment, the expression vector is a DNA which comprises a first DNA sequence which is a phage DNA portion encoding bacteriophage integration into a mutated mycobacterium chromosome, and a second DNA sequence which encodes the complement gene, and may further include a third DNA sequence encoding at least one protein or polypeptide which is heterologous to the mutated mycobacterium in which the DNA is to be integrated.

The term "phage DNA portion," as used herein means that the DNA sequence is derived from a phage and lacks the DNA which is required for phage replication.

Bacteriophages from which the phage DNA portion may be derived include, but are not limited to, mycobacteriophages, such as but not limited to the L5, L1, Bxb1, Bxb2, Bxb3, D29, and TM4 mycobacteriophages; the lambda phage of *E. coli*; the toxin phages of Corynebacteria; phages of Actinomyces and Norcadia, the O/C31 phage of Streptomyces; and the P22 phage of Salmonella. Preferably, the phage DNA portion encodes mycobacteriophage integration into a mycobacterium chromosome.

Preferably, the first DNA sequence includes DNA encoding integrase, which is a protein that provides for integration of the DNA into the mutated *M. bovis* or mutated *M. bovis*-BCG or mutated *M. tuberculosis* or mutated *M. leprae* mycobacterial chromosome. Most preferably, the first DNA sequence also includes DNA which encodes an attP site.

The DNA sequence encoding the attP site, and the integrase provides for an integration event which is referred to as site-specific integration. DNA containing the attP site and the integrase gene is capable of integration into a corresponding attB site of an *M. bovis*-BCG, *M. tuberculosis*, or *M. leprae* chromosome.

It is to be understood that the exact DNA sequence encoding the attP site may vary among different phages, and that the exact DNA sequence encoding the attB site may vary among *M. bovis*, *M. bovis*-BCG, *M. tuberculosis*, and *M. leprae*.

The integration event results in the formation of two new junction sites called attL and attR, each of which contain part of each of attP and attB. The inserted and integrated non-phage DNA which includes the first, second, and preferably third DNA sequences, is flanked by the attL and attR sites. The insertion and integration of the phage DNA portion results in the formation of a transformed mutated mycobacterium which includes an insertionally mutated mycobacterial gene, a complement gene, and preferably a DNA sequence which encodes a protein or polypeptide which is heterologous to mycobacteria.

The third DNA sequence which encodes a protein or polypeptide heterologous to mycobacteria may be DNA which is all or a portion of a gene encoding protein(s) or polypeptide(s) of interest, such as those hereinabove described; DNA encoding a selectable marker or markers; or DNA encoding both a selectable marker or markers and at least one protein or polypeptide of interest.

Selectable markers which may be encoded include, but are not limited to, the kanamycin resistance marker, the neomycin resistance marker, the chloramphenicol resistance marker, the hygromycin resistance marker, or a bacteriophage resistance marker, such as those hereinabove described.

The phage DNA portion, which includes the first DNA sequence encoding mycobacterium phage integration, and the second DNA sequence encoding the complement gene, and the third DNA sequence, if present, encoding at least one protein or polypeptide heterologous to mycobacteria, may be constructed through genetic engineering techniques known to those skilled in the art. In one embodiment, the phage DNA portion may be a plasmid including, in addition to the DNA encoding integration, the DNA encoding the complement gene, and, if present, the DNA encoding a heterologous protein, an origin of replication for any of a wide variety of organisms which includes, but is not limited to, *E. coli,* Streptomyces species, Bacillus species, Staphylococcus species, Shigella species, Salmonella species, and various species of pneumococci. Preferably the plasmid includes an origin of replication for *E. coli*.

The phage DNA portion also may include a suitable promoter. Suitable promoters include, but are not limited to, mycobacterial promoters such as the BCG HSP60 and HSP70 promoters; mycobactin promoters of *M. tuberculosis* and BCG, the superoxide dismutase promoter, the α-antigen promoter of *M. tuberculosis* and BCG, the MBP-70 promoter, the 45 kda antigen promoter of *M. tuberculosis* and BCG; the mycobacterial asd promoter; the mycobacterial 14 kda and 12 kda antigen promoters; mycobacteriophage promoters such as the Bxb1, Bxb2, and Bxb3 promoters, the L1 and L5 promoters, the D29 promoter, and the TM4 promoters; *E. coli* promoters; or any other suitable promoter.

The selection of a suitable promoter is deemed to be within the scope of those of ordinary skill in the art from the teachings contained herein.

The promoter sequence may, in one embodiment, be part of an expression cassette which also includes a portion of the gene normally under the control of the promoter. For example, when a mycobacterial HSP60 or HSP70 promoter is employed, the expression cassette may include, in addition to the promoter, a portion of the gene for the HSP60 or HSP70 protein. When the expression cassette and the DNA encoding a heterologous protein or polypeptide are expressed, the protein expressed by the cassette and the DNA encoding the heterologous protein or polypeptide is a fusion protein of a fragment of a mycobacterial protein (e.g., the HSP60 or HSP70 protein), and of the heterologous protein.

Preferably, the transcription initiation site, the ribosomal binding site, and the start codon, which provides for the initiation of the translation of mRNA, are each of mycobacterial origin. The stop codon, which stops translation of mRNA, thereby terminating the synthesis of the complement protein and/or the heterologous protein, and the transcription termination site, may be of mycobacterial origin, or of other bacterial origin, or such stop codon and transcription termination site may be those of the DNA encoding the complement gene or DNA encoding the heterologous protein or polypeptide, when such DNA is present.

Such DNA which includes a first DNA sequence which is a phage DNA portion encoding bacteriophage integration into a mycobacterium chromosome, and a second DNA sequence encoding a complement gene, and if present, a third DNA sequence encoding at least one protein or polypeptide which is heterologous to the mutated mycobacterium in which the DNA is to be integrated is further described in application Ser. No. 553,907, filed Jul. 16, 1990, the contents of which are hereby incorporated by reference.

In another embodiment, the expression vector includes DNA which encodes the complement gene, and may further include DNA which encodes a protein or polypeptide heterologous to the mutated mycobacterium which expresses the protein or polypeptide, such as those hereinabove described, and a promoter selected from the class consisting of mycobacterial promoters and mycobacteriophage promoters for controlling expression of the DNA encoding the complement gene and, if present, the DNA encoding the heterologous protein or polypeptide. The mycobacterial promoters may be those as hereinabove described with respect to the DNA which encodes phage integration into a mycobacterium chromosome. The promoter may also be part of an expression cassette which also includes a portion of the gene normally under the control of the promoter, as hereinabove described. Also, the transcription initiation codon, the ribosomal binding site, and the start codon, may each be of mycobacterial origin, and the stop codon, and the transcription termination site, may be of mycobacterial origin, or of other bacterial origin, or the stop codon and transcription termination site may be those of the DNA encoding the complement gene, or of the DNA encoding the heterologous protein or polypeptide, also as hereinabove described.

In one embodiment, the mycobacterial promoter is a BCG promoter.

In another embodiment, the heterologous protein or polypeptide may be a selectable marker. Such selectable markers include, but are not limited to, the B-galactosidase marker, the kanamycin resistance marker, the chloramphenicol resistance marker, the neomycin resistance marker, the hygromycin resistance marker, or a bacteriophage resistance marker such as those hereinabove described.

In one embodiment, the expression vector further includes a mycobacterial origin of replication.

In accordance with another embodiment, such an expression vector may be a plasmid. The plasmid may be a non-shuttle plasmid, or may be a shuttle plasmid which further includes a bacterial origin of replication such as an E. coli origin of replication, a Bacillus origin of replication, a Staphylococcus origin of replication, a Streptomyces origin of replication, or a pneumococcal origin of replication.

The vector may further include a multiple cloning site, and the DNA encoding for the complement gene and/or the DNA encoding for the heterologous protein is inserted in the multiple cloning site.

Such an expression vector including a mycobacterial promoter or a mycobacteriophage promoter is further described in application Ser. No. 642,017, filed Jan. 16, 1991, which is a continuation of application Ser. No. 552,828, filed Jul. 16, 1990, now abandoned. The contents of application Ser. No. 642,017 are hereby incorporated by reference.

In another embodiment, the expression vector which includes the complement gene and/or DNA encoding for a protein or polypeptide which is heterologous to mycobacteria is a shuttle plasmid vector, which replicates as a plasmid in bacteria and as a phage in mycobacteria. In one embodiment, the shuttle plasmid vector includes two species of cohesive end sites: one for lambda phage, which functions in E. coli; and one for mycobacteria (eg., the mycobacteriophage TM) which functions in mycobacteria. Preferably, such shuttle plasmid vector has a unique site (eg., a unique EcoRI site) into which the complement gene and/or DNA encoding a protein or polypeptide heterologous to mycobacteria may be inserted. Examples of such shuttle plasmid vectors are further described in application Ser. No. 361,944, filed Jun. 5, 1989 the contents of which are hereby incorporated by reference.

It is also to be understood that within the scope of the present invention, the complement gene may be contained in one expression vector, and a gene encoding a protein or polypeptide heterologous to mycobacteria may be contained in another expression vector.

It is also another object of the present invention to effect mutations in mycobacteria, such as M. bovis, M. bovis-BCG, M. tuberculosis, M. avium, or M. smegmatis, in order to change the properties of such mycobacteria through the use of a transposon or a vector which includes a pair of inverse repeat elements and a DNA sequence encoding a transposase. Preferably, the transposon is the IS1096 transposon of M. smegmatis, and when a vector including a pair of inverse repeat elements and a DNA sequence encoding a transposase is employed, the inverse repeat elements and the DNA sequence encoding a transposase are the inverse repeat elements and the transposase sequence of IS1096.

In a preferred embodiment, the transposon or vector is constructed such that the transposon or vector further includes a selectable marker such as those hereinabove described. Thus, one may transfect the transposon, or the vector containing the inverse repeat sequences and the DNA encoding the transposase into mycobacteria, and subsequent to such transfection, may screen the mycobacteria for presence of the selectable marker, thereby selecting those mycobacteria in which the transposon and selectable marker, or the pair of inverted repeat sequences and selectable marker, have inserted randomly into the mycobacterial chromosome. Once it has been determined that the transposon and selectable marker or the inverse repeat sequences and selectable marker have inserted randomly into the mycobacterial chromosome, the mycobacteria may be screened to determine the gene(s) which is mutated.

In another embodiment, the transposon, or vector including a pair of inverse repeat sequences further includes at least one DNA sequence which encodes a protein or polypeptide heterologous to mycobacteria. The proteins or polypeptides may be those hereinabove described, and such DNA sequence may be under the control of a suitable promoter, such as those hereinabove described.

Thus, in accordance with another aspect of the present invention, there is provided a mycobacterial transposon, or portion thereof, which is capable of inserting randomly into a mycobacterial chromosome to effect an insertional mutation of a mycobacterial gene. The mycobacterial transposon may, for example, insert randomly into an *M. bovis* chromosome, an *M. bovis*-BCG chromosome, an *M. tuberculosis* chromosome, an *M. avium* chromosome, an *M. leprae* chromosome, or an *M. smegmatis* chromosome. In one embodiment, the transposon is the IS1096 transposon of *M. smegmatis* or portion of derivative thereof. The IS1096 transposon, which is hereinafter described, is 2,275 bp in length, and contains two open reading frames which may encode proteins involved in transposition. Although the IS1096 transposon is found in *M. smegmatis*, it is contemplated that the transposon may be employed in generating insertional mutations in other species of mycobacteria, such as those hereinabove mentioned.

The term "transposon" as used herein, means a non-mutated transposon or a mutated transposon in which a portion of the transposon sequence has been deleted and/or replaced, and/or wherein the transposon contains additional DNA sequence(s).

In general, a transposon contains an inverted repeat sequence at each (5' and 3') end, and a gene(s) encoding a transposase enzyme(s) between the inverted repeat sequences. The transposase(s) acts upon the inverted repeat sequences so as to enable the transposon to remove itself from a DNA (eg., chromosomal DNA, plasmid DNA, phage DNA, etc.) and insert or transpose into another DNA, or into another region of the same DNA. In some instances, the transposon may also include gene(s) encoding resolvase(s) and/or regulatory protein(s) which regulate transposition.

The insertional mutation, which is effected by a mycobacterial transposon, may be effected by random transposition, or "hopping" of a transposon contained in a mycobacterial chromosome from one region of the chromosome into a mycobacterial gene contained in another region of the chromosome, or the transposon may be transfected into the mycobacterium by a variety of means. Subsequent to transfection, the transposon may then insert at random into the mycobacterial chromosome to effect an insertional mutation.

The transposon may be contained in any plasmid or phage DNA vector, including mycobacterial vectors and mycobacteriophage vectors. In one embodiment, the transposon may be contained in a mycobacterial vector. The vector may include a mycobacterial promoter or mycobacteriophage promoter, such as those hereinabove described. In another embodiment, the transposon may be contained within a mycobacterial expression vector or DNA which encodes phage integration into a mycobacterium chromosome, such as hereinabove described, or the transposon may be contained within phage DNA which can replicate within one organism, but not within the organism into which the phage is transfected. Alternatively, the transposon may be contained in a conjugative plasmid which can replicate in a bacterium other than a mycobacterium but cannot replicate in mycobacteria. For example, the transposon may be contained in a conjugative plasmid which can replicate in a bacterium such as *E. coli* or Streptomyces, but cannot replicate in *M. bovis*-BCG.

In one embodiment, a mycobacterial transposon may be constructed which includes at least one DNA sequence which encodes a protein heterologous to mycobacteria. The at least one DNA sequence which encodes a protein heterologous to mycobacteria may be DNA which is all or a portion of a gene encoding protein(s) or polypeptide(s) of interest. The proteins or polypeptides of interest may be those hereinabove described. The at least one DNA sequence which encodes a protein heterologous to mycobacteria may be under the control of a suitable promoter. Such a transposon may be constructed by techniques known to those skilled in the art. The transposon may also include transposase gene(s) and/or a selectable marker such as those hereinabove described.

In accordance with another aspect of the present invention, there is provided a vector for inserting DNA into the chromosome of a mycobacterium and in particular for mutating at least one gene of the mycobacterium. The vector includes a pair of inverted repeat sequences and DNA encoding a transposase. In one embodiment, the inverted repeat sequences and the transposase sequence are the inverted repeat sequences and transposase sequence of transposon IS1096. The transposase sequence for IS1096 is shown in FIG. 29 and is indicated therein as tnpA. The 5' and 3' inverted repeat sequences of IS1096 are shown in FIG. 29 in bold type.

In another embodiment, the vector further includes DNA encoding resolvase, which also may be a DNA resolvase sequence of transposon IS1096.

In a preferred embodiment, the vector further includes a DNA sequence encoding a heterologous protein (or polypeptide). Such heterologous proteins may be antigens, anti-tumor agents, enzymes, lymphokines, pharmacologic agents, immunopotentiators, or reporter molecules of interest, as hereinabove described or, the heterologous protein is preferably a selectable marker also as hereinabove described to identify mycobacteria having the transposon or portion thereof inserted into the chromosome to enable identification of mutants. The DNA sequence which encodes a heterologous protein or polypeptide is placed between the inverted repeat sequences of the vector. Such DNA sequence encoding the heterologous protein or polypeptide may be placed at any position between the internal repeat sequences, as long as the DNA encoding the heterologous protein or polypeptide is not placed within the DNA encoding the transposase.

In one embodiment, the transposase is located 3' to the 5' inverted repeat sequence, and 5' to the 3' inverted repeat sequence. In such an embodiment, a DNA sequence which encodes a heterologous protein or polypeptide may be placed between the 5' inverted repeat and the transposase sequence, and/or may be placed between the transposase and the 3' inverted repeat sequence. The vector then may be transfected into a mycobacterium, whereby the transposable element, which includes the inverse repeats sequences, the DNA sequence which encodes a heterologous protein, and the transposase, inserts randomly into a mycobacterium chromosome.

In another embodiment, the transposase is located 5' to the 5' inverted repeat sequence (i.e., outside the inverted repeat sequences). The at least one DNA sequence encoding a heterologous protein is located 3' to the 5' inverted repeat and 5' to the 3' inverted repeat.

Mycobacteria may be transformed with plasmids or vectors containing transposition elements in which the order of sequences has been modified, for example, where the transposase enzyme gene has been moved exterior to the inverted repeat sequences, preferably upstream from the 5 inverted repeat sequence. Optionally, the vector may have between the inverted repeat sequences a heterologous gene which will be expressed once integrated into the mycobacterial chromosome. The vector then may be transfected into a mycobacterium. Because the transposase coding sequence is exterior to the inverted repeat sequences, when the inverted sequences and those sequences between them are caused to "hop" from the plasmid to integrate into the mycobacterial chromosome, the transposase gene is not carried along with this element. Therefore, the construct that is caused to transfer and integrate into the mycobacterial genome is considerably more stable, i.e., it no longer possesses the capability to "hop," than would conventional transposon elements, even though it is carrying resistance marker genes or other such heterologous elements. Mycobacteria transformed with transposon IS1096 derivatives, such as those described above, are a significant aspect of the invention in that they are more stable than conventional transposon mutated mycobacteria. For the purposes of this invention, transposons which have been so modified structurally are sometimes hereinafter referred to as "derivatives" of the native transposon.

In one embodiment, a construct may be formed in which the transposase gene(s), and resolvase gene(s) and/or regulatory protein gene(s) if present, is removed from a mycobacterial transposon and placed outside the inverted repeat sequences, and the at least one DNA sequence encoding a protein heterologous to the mycobacterium, and preferably a selectable marker, is placed between the inverted repeat sequences. The construct may then be placed into a vector, which may be as hereinabove described, for transfection into a mycobacterium. The transposable element, containing the inverted repeat sequences, the at least one DNA sequence encoding the protein or polypeptide heterologous to the mycobacterium, and the selectable marker, may then insert randomly into the mycobacterium chromosome.

In one embodiment, a construct is made in which the gene(s) encoding a transposase(s) and gene(s) encoding resolvase(s) and/or regulatory protein(s) if also present, is removed from its normal position in the transposon (between the inverted repeat sequences), and is placed, in the resulting construct, outside the inverted repeat sequences. A gene encoding a heterologous protein, such as, for example, a selectable marker, such as those hereinabove described (e.g., antibiotic resistance, such as, for example, a kanamycin resistance gene) is then placed between the inverted repeat sequences. The transposable element thus includes the inverted repeat sequences and the selectable marker. This construct is then cloned into a mycobacterial expression vector which includes a mycobacterial origin of replication and may also include a mycobacterial promoter or mycobacteriophage promoter such as those hereinabove described. The mycobacterial origin of replication of the plasmid is then mutated such that the mycobacterial origin of replication becomes temperature sensitive (eg., the plasmid can replicate at 30° C. but not at 37° C.). The plasmid is then transfected into mycobacteria at 30° C., and the mycobacteria are selected for antibiotic resistance. Antibiotic resistant colonies are then plated out on complete medium containing the antibiotic at 37° C. At 37° C., the plasmid containing the mutated mycobacterial origin of replication cannot replicate. Those mycobacteria which survive are those in which the transposable element containing the inverted repeat sequences and the antibiotic resistance marker has transposed from the plasmid into the mycobacterial chromosome. Because the transposase gene(s), as well as resolvase gene(s) and/or regulatory protein gene(s), if present, remains in the plasmid, the transposase gene(s) as well as resolvase and/or regulatory protein gene(s), if present, is lost upon further replication of the mycobacteria, and, therefore, the transposed construct, upon insertion into the mycobacterial chromosome, will not undergo any subsequent transpositions.

Alternatively, the construct hereinabove described may be cloned into a vector which cannot replicate in mycobacteria; i.e., the vector does not include a mycobacterial origin of replication. The vector is then transfected into mycobacteria. Because the vector containing the construct cannot replicate in mycobacteria, the vector will become lost. The mycobacteria, after transfection, are screened for antibiotic resistance. Those mycobacteria which survive are those in which the transposable element containing the inverted repeat sequences and the antibiotic resistance marker has transposed from the plasmid into the mycobacterial chromosome. The transposase gene(s), plus resolvase and/or regulatory protein gene(s), if present, remains in the plasmid, and therefore is lost upon further replication of the mycobacteria, and, therefore, the transposed construct, upon insertion into the mycobacterial chromosome, will not undergo further transpositions.

Once the insertional mutation of a mycobacterial gene is effected by a mycobacterial transposon, or by a vector including at least a pair of inverse repeat sequences and DNA encoding a transposase, the mycobacteria may be screened to determine the gene(s) which is mutated, by methods hereinabove described. Once the mutated gene is identified, the complement gene may be isolated and cloned into an expression vector which is transformed into the mutated mycobacterium.

It is also contemplated within the scope of the present invention that insertional mutations may be generated in M. tuberculosis of gene(s) conferring virulence upon M. tuberculosis, thereby transforming M. tuberculosis from a pathogenic to a non-pathogenic organism. Such mutated non-pathogenic M. tuberculosis organisms may be employed in a vaccine for protection against tuberculosis. If desired, the mutated non-pathogenic M. tuberculosis organisms may be subjected to further insertional mutagenesis, as hereinabove described, whereby auxotrophy may be conferred upon the mutated M. tuberculosis organisms. Such mutated M. tuberculosis organisms may then be genetically engineered through techniques such as those hereinabove described, so as to express the complement gene and/or genes for heterologous proteins of interest, such as those hereinabove described.

The mutated mycobacteria hereinabove described, which are transformed with DNA which encodes a protein(s) or polypeptide(s) heterologous to mycobacteria may be employed in the production of a vaccine or therapeutic agent, depending upon the protein(s) or polypeptide(s) expressed by the transformed mutated mycobacteria.

To form such a vaccine or therapeutic agent, the transformed mutated mycobacteria are administered in conjunction with a suitable pharmaceutical carrier. As representative examples of suitable carriers there may be mentioned: mineral oil, alum, synthetic polymers, etc. Vehicles for vaccines and therapeutic agents are well known in the art and the selection of a suitable vehicle is deemed to be within the scope of those skilled in the art from the teachings contained herein. The selection of a suitable vehicle is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration.

Other means for administering the vaccine or therapeutic agent should be apparent to those skilled in the art from the teachings herein; accordingly, the scope of the invention is not to be limited to a particular delivery form. When the transformed mutated mycobacteria are employed as a vaccine, such a vaccine has important advantages over other presently available vaccines. Mycobacteria have, as hereinabove indicated, adjuvant properties among the best currently known and, therefore, stimulate a recipient's immune system to respond with great effectiveness. This aspect of the vaccine induces cell-mediated immunity and thus is especially useful in providing immunity against pathogens in cases where cell-mediated immunity appears to be critical for resistance. Also, mycobacteria may stimulate long-term memory or immunity. It thus may be possible to prime long-lasting T cell memory, which stimulates secondary antibody responses neutralizing to the infectious agent or the toxin. Such priming of T cell memory is useful, for example, against tetanus and diphtheria toxins, pertussis, malaria, influenza virus, Herpes virus, rabies, Rift Valley Fever virus, dengue virus, measles virus, Human Immunodeficiency Virus (HIV), respiratory syncytial virus, human tumors, and snake venoms. Another advantage in employing mycobacteria transformed in accordance with the present invention as a vaccine or a therapeutic agent is that mycobacteria in general have a large genome (i.e., approximately $3 \times 10^6$ base pairs in length). Because the genome is large, it is able to accommodate a large amount of DNA from other source(s), and may possibly be employed to make a vaccine and/or therapeutic agent containing DNA sequences encoding more than one antigen and/or therapeutic agent.

The invention will now be described with respect to the following examples; however, the scope of the present invention is not intended to be limited thereby.

EXAMPLE 1 (COMPARATIVE)

Random Shuttle Mutagenesis of M. smegmatis

Figure 2:
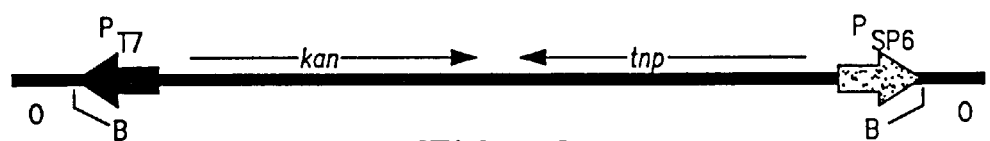
FIG. 2. Representation of transposon Tn5 seq 1.
Figure 13:
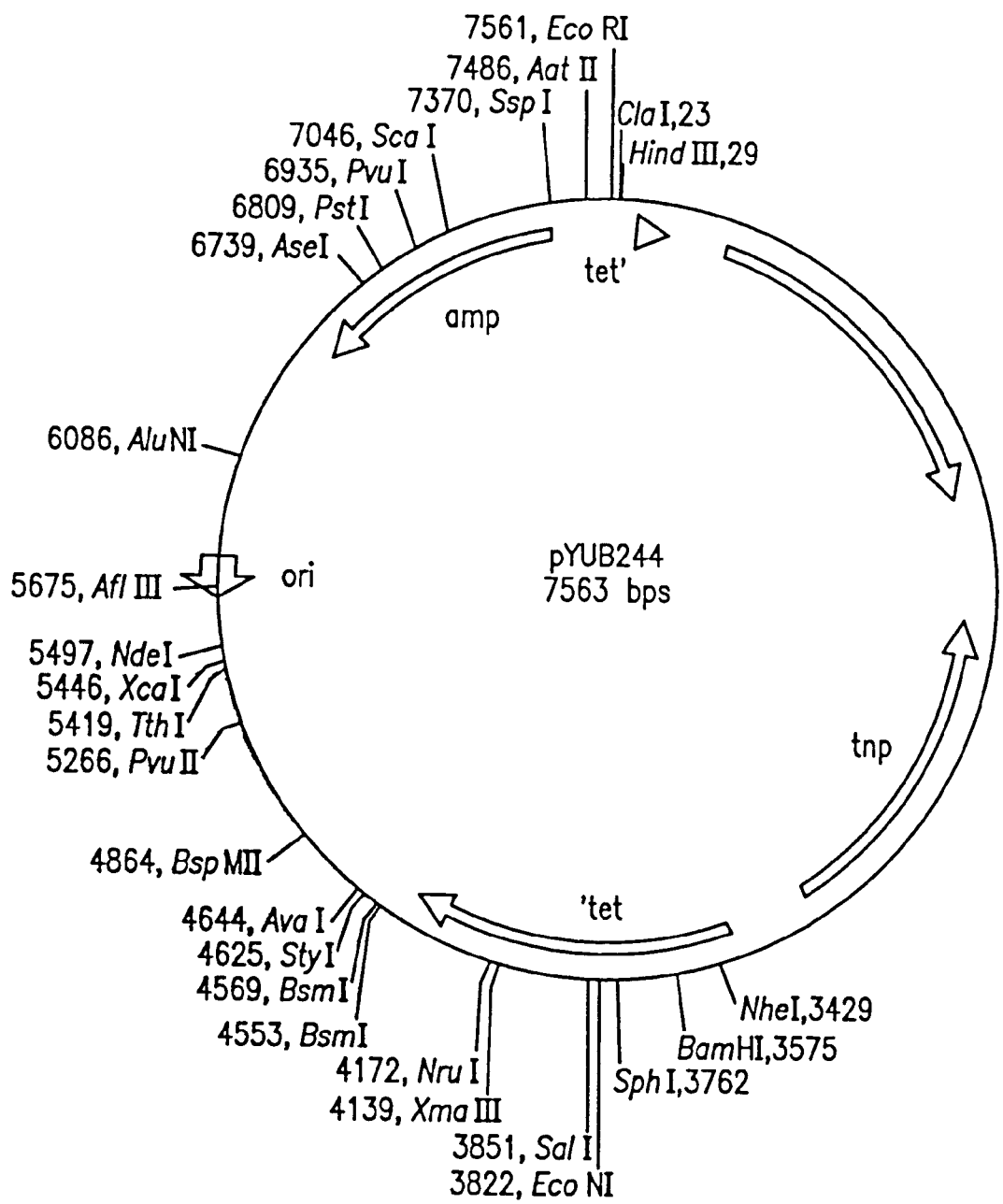
FIG. 13. Representation of plasmid pYUB244.

Chromosomal DNA of M. smegmatis strain mc$^2$6 (Jacobs, Jr., et al. Nature, Vol. 327, pgs. 532–536 (1987)) was partially digested with Msp I. Following size selection, DNA inserts of 4 kb to 7 kb were ligated to Cla I-digested pYUB36 (FIG. 1). pYUB36 includes a gene (amp) for ampicillin resistance, and an E. coli origin of replication, and is a derivative of pBR 322 (Bolivar, et al., Gene, Vol. 2, pgs. 95–113 (1977) in which a nonessential 1.9 kb EcoRV to Pvu II fragment has been deleted. After the DNA inserts have been ligated to ClaI-digested pYUB36, the resulting constructs are transformed into E. coli strain ec$^2$ 270, a derivative of E. coli strain X 2338 (Jacobs, et al., Proc. Natl. Acad. Sci., Vol. 83, pgs. 1926–1930 (1986)) into which transposon Tn5 seq 1 (Nag., et al., Gene, Vol. 64, pgs. 135–145 (1988)) (FIG. 2) is inserted at an unknown location of the chromosome. Tn5 Seq 1 encodes the neo gene which confers kanamycin resistance to both E. coli and mycobacteria (Snapper, et al., Proc. Natl. Acad. Sci., Vol. 85, pgs. 6987–6991 (1988)), permits selection of insertions into DNA sequences cloned into plasmid vectors using its neomycin hyper-resistance phenotype (Berg, et al., Genetics, Vol. 105, pgs. 813–828 (1983)), and Tn5seq1 lacks the cryptic gene present in Tn5 which encodes streptomycin resistance, which is an important biohazard consideration for the genetic engineering of M. tuberculosis strains as hereinafter described. (U.S. Fed. Register, Vol. 51, pg. 16957). The transformed E. coli organisms are plated on L-agar medium containing both ampicillin and kanamycin at concentrations of 40 µg/ml and 50 µg/ml, respectively. About 30,000 individual transformants were pooled and samples were diluted $10^{-3}$ into 20 independent 5 ml cultures and incubated at 37° C. overnight. A 200 µl sample from each overnight culture yielded approximately 1000 colonies on L-agar containing 250 µg/ml neomycin, whereby such colonies were selected for neomycin hyper-resistance, which is conferred through transposition of Tn5 seq 1 from the E. coli chromosome into the transfecting plasmids. Plasmid DNA from the neomycin hyper-resistant colonies was isolated as described in Birnboim, Methods in Enzymology, Vol. 100, pgs 243–255 (1983), and was re-transformed into E. coli strain X2338, and plasmid DNA was subsequently isolated and prepared from the transformants. The Tn5 seq 1-mutagenized plasmid library was then electroporated into either M. smegmatis strain mc$^2$6 or M. smegmatis strain mc$^2$155 (Snapper, et al., Mol. Microbiol., Vol. 4, pgs. 1911–1919 (1990)), and kanamycin-resistant transformants were selected on K-agar (Middlebrook 7H10 agar supplemented with 5 mg/ml casamino acids (Difco), 100 µg/ml diaminopimelic acid, 50 µ/ml thymidine, 40 µg/ml uracil, 133 µg/ml adenosine, 0.2% glycerol, albumen-dextrose complex, and 10 µg/ml cyclohexamide) containing 20 µg/ml kanamycin. Kanamycin resistant transformants were obtained at a frequency of 20 to 40 per µg of plasmid DNA. No kanamycin resistant colonies were obtained with a control pBR322::Tn5seq 1 plasmid (also known as pYUB244, as shown in FIG. 13) which lacked homologous DNA sequences. About 800 individual M. smegmatis transformants were screened for auxotrophy by streaking onto minimal Sauton medium without asparagine. The transformants were screened for auxotrophy as described in Davis, et al., A Manual for Genetic Engineering: Advanced Bacterial Genetics, Cold Spring Harbor Laboratory (1980), Appendix 2, pgs. 209–210. Three auxotrophs were obtained from this screen and their nutritional requirements were determined by plating on Sauton agar plates supplemented with one or the other of 11 pools of nutrients used for the auxanography analysis of E. coli as described in Davis, et al. (1980). The auxotrophs obtained by this screen were a methionine-requiring auxotroph (M. smegmatis strain mc$^2$311), a pyridoxine-requiring auxotroph (M. smegmatis strain mc$^2$313), and an auxotroph which is incompletely characterized.

EXAMPLE 2

Figure 3:
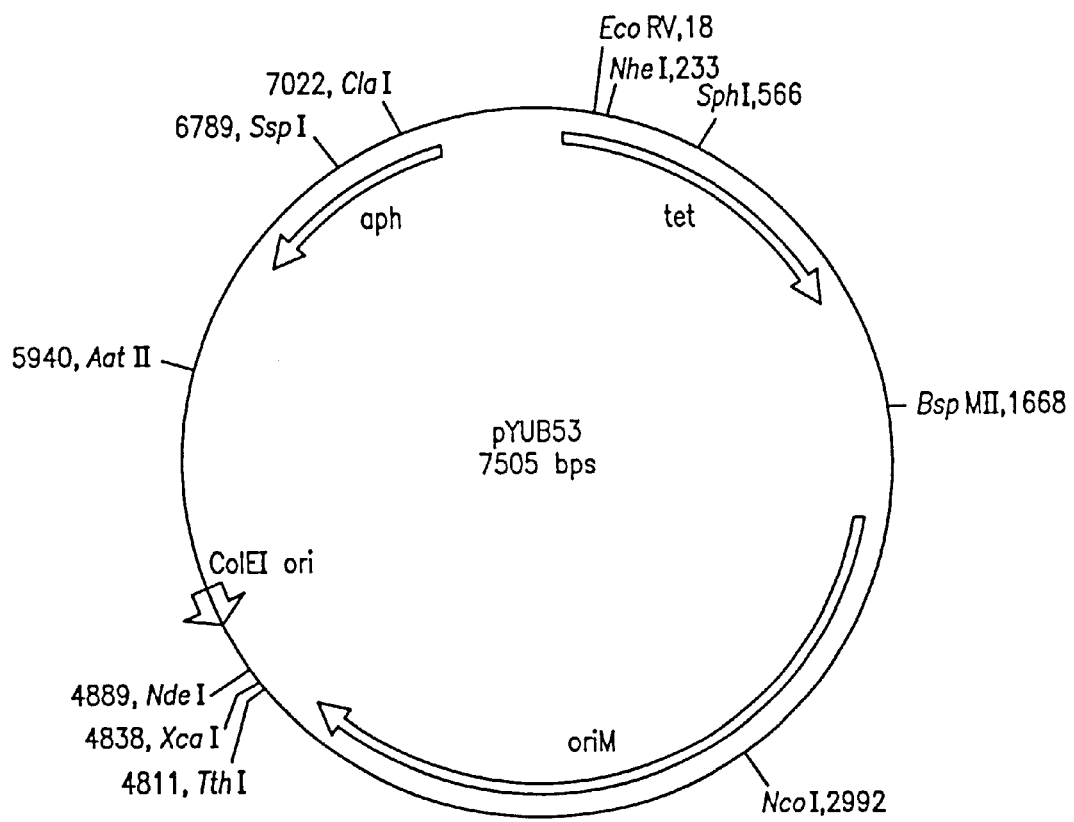
FIG. 3. Representation of plasmid pYUB53.

A. Isolation of BCG Pasteur Complementing Clones of M. smegmatis Methionine Auxotroph A genomic library of BCG Pasteur (obtained from the WHO BCG Reference Laboratory at the Statens Seruminstitut in Copenhagen) was constructed by ligating 4 kb–7 kb Msp-I digested chromosomal DNA fragments to ClaI-digested pYUB53 (FIG. 3), an E. coli/mycobacteria shuttle vector including an E. coli origin of replication and a mycobacterial origin of replication. Ligated DNA's were then introduced into *E. coli* strain ec²270, and plasmids isolated from the pool of *E. coli* as described in Snapper, et al. (1988), were electroporated into the *M. smegmatis* methionine auxotroph, mc²311. Such plasmids, because they include a mycobacterial origin of replication, do not integrate into the mycobacterial chromosome, but self-replicate within the mycobacterium. Plasmids which conferred prototrophy to mc²311 (referred to as met-complementing clones) were isolated as described in *Snapper*, et al. (1988)

B. Inactivation of Met-Complementing Clones

The met-complementing clone, named pYUB121, underwent insertional inactivation in *E. coli* by neomycin hyper-resistance selection as hereinabove described in Example 1. Individual pYUB121 clones were then screened for the loss of their ability to complement the methionine auxotrophic mutation of mc²311 according to the procedure described in Davis, et al. (1980).

C. Recombination in BCG.

Figure 4:
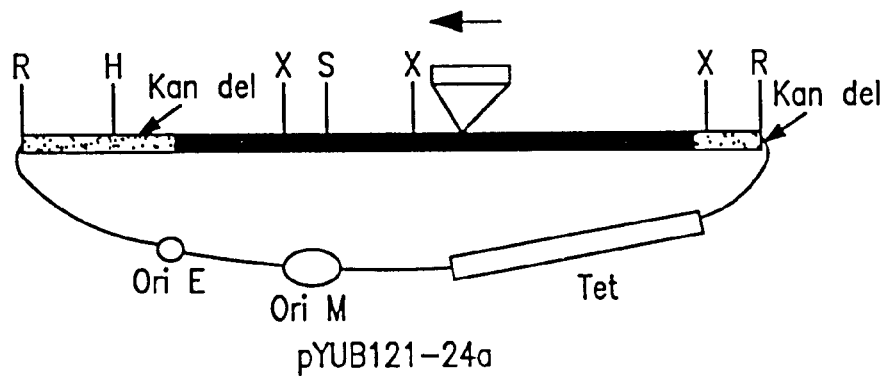
Figure 5:
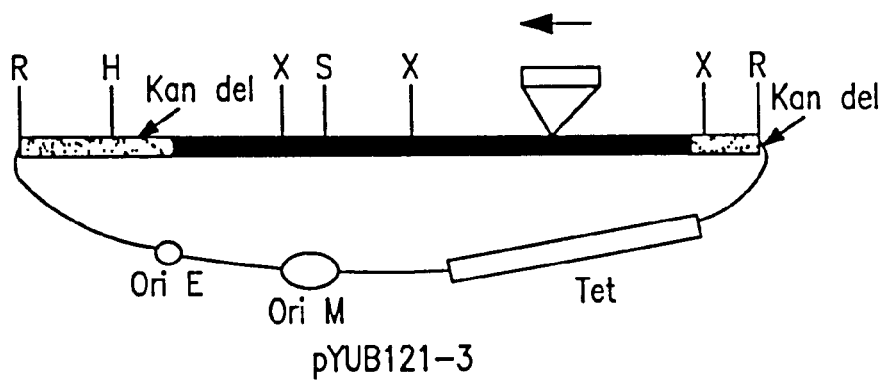
FIG. 5. Representation of plasmid pYUB121-3.
Figure 6:
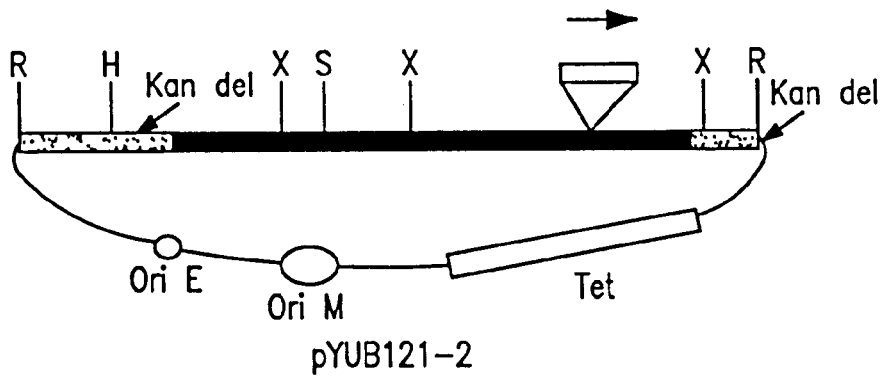
FIG. 6. Representation of plasmid pYUB121-2.
Figure 7:
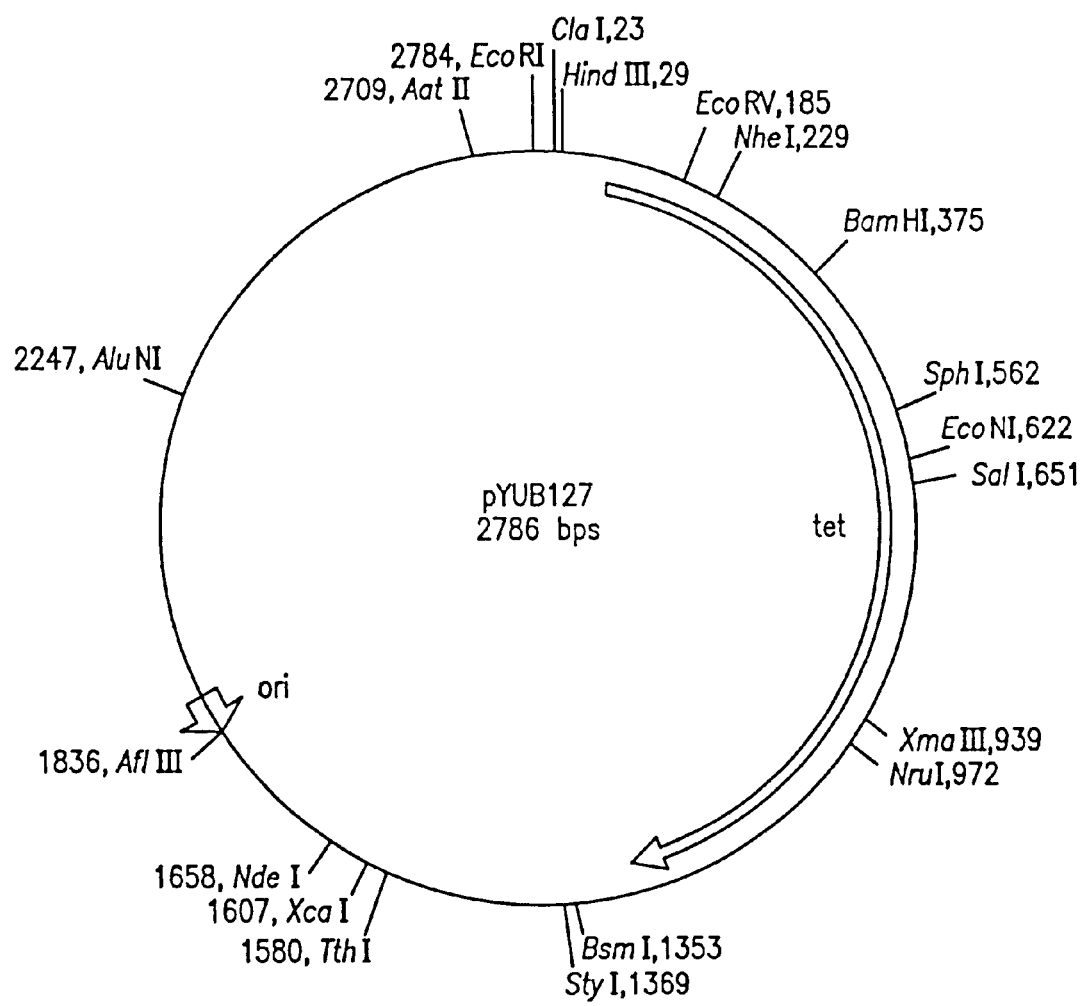
FIG. 7. Representation of plasmid pYUB127.

Plasmids pYUB121.24a (FIG. 4), pYUB121.3 (FIG. 5), and pYUB121.2 (FIG. 6) were isolated from methionine auxotrophic mutants of mc²311 according to the procedure of *Snapper*, et al. (1988). Each of pYUB121.24a, pYUB121.3, and pYUB121.2 was digested with EcoRI. The EcoRI fragments containing Tn5seq1 from each plasmid were subcloned into EcoRI digested pYUB127 (FIG. 7), an *E. coli* vector incapable of replicating in mycobacteria, to obtain the corresponding plasmids pYUB149 (FIG. 8), pYUB147 (FIG. 9), and pYUB146 (FIG. 10), respectively.

BCG-Pasteur was electroporated as described in Bernardini, et al. *Proc. Natl. Acad. Sci.*, Vol. 86, pgs. 3867–3871 (1989) with pYUB146, but with the following modifications. BCG cultures were subcultured 1:50 in 50 ml MADC-TW broth (Snapper, et al., *Proc. Natl. Acad. Sci.*, Vol. 85, pgs. 6987-6991 (1988)) and grown for 10 days at 37° C. The harvested culture was washed first with 50 ml and then with 25 ml of cold glycerol. Following centrifugation, the final pellet was resuspended in 2.5 ml of cold 10% glycerol and 0.4 ml used for each electroporation. BCG transformants were plated on Middlebrook 7H10 agar supplemented with albumin-dextrose complex (ADC), 0.2% glycerol, and 10 µg/ml cyclohexamide containing kanamycin (20 µg/ml) and methionine (50 µg/ml), as described in *Snapper*, et al. (1988).

It was expected that homologous recombination resulting from a double crossover event, of a linear DNA fragment containing the Tn5 seq 1-inactivated methionine gene would yield kanamycin resistant, methionine auxotrophs of BCG. Unexpectedly, only one methionine auxotroph of over 200 kanamycin-resistant transformants of BCG-Pasteur was obtained from the transformation of linearized pYUB146 containing a Tn5 seq 1-inactivated methionine gene. The transformants were screened according to the procedure of *Davis*, et al., (1980). Such a result indicates that a high degree of illegitimate, or random recombination has occurred in the transformed BCG-Pasteur organisms in that the Tn5 seq 1 inactivated met gene did not recombine, or integrate, into the homologous met site in the BCG chromosome.

EXAMPLE 3

Demonstration of Illegitimate Recombination in BCG

Total chromosomal DNA from the BCG methionine auxotroph obtained in Example 2, sometimes hereinafter referred to as BCG strain mc² 576, deposited as ATCC No. 55202, and from two other kanamycin-resistant transformants was subjected to Southern blot analysis using the 1.8 kb XhoI DNA fragment from the BCG met gene as a probe. (FIG. 11). This probe detects an 8.5 kb fragment in the wild-type BCG chromosome, as shown in Lane 1 of FIG. 11. If homologous recombination had taken place, a double cross-over between the chromosome and the linear DNA from the transforming plasmid should result in the replacement of the chromosomal met gene by the insertionally inactivated gene. In Southern blot analysis, the 8.5 kb XhoI fragment of the chromosome should be replaced by two new XhoI fragments, due to the presence of an XhoI site in Tn5 seq 1. The total length of the two fragments should be 8.5 kb plus 3.2 kb, with 3.2 kb being the size of Tn5 seq 1. As shown in FIG. 11, however, the auxotroph, mc²576 (lane 2), as well the two other kanamycin-resistant transformants (lanes 3 and 4), contained three XhoI fragments, one 8.5 kb fragment and two fragments A and B, which are identical to that present in the Tn5 seq 1 inactivated BCG met clone. These results indicated that no double cross-over occurred either in the methionine auxotroph, mc² 576 or the two other kanamycin-resistant transformants. Therefore, it is likely that the linear DNA fragment containing the Tn5seq 1 inactivated met gene has integrated illegitimately into the BCG chromosome.

Southern analysis was also performed using Hind III digested chromosomal DNA and the same XhoI met probe. Analysis of wild type BCG detects only one fragment (FIG. 11, lane 5). As shown in FIG. 11, the internal Hind III fragment C of the donor (plasmid) DNA is conserved in all three clones (lanes 6, 7 and 8). Southern analysis of Hind III digested chromosomal DNA with the probe also detects a flanking fragment D, indicated by an asterisk (*) in the auxotroph (lane 6), and the prototrophs (lanes 7 and 8), the size of which depends upon the site of integration. The variation in size of the flanking fragment D from different BCG recombinants again indicates that the donor, or transforming, DNA fragment is integrating randomly into the BCG chromosome. Also, the Southern blots of XhoI and Hind III digested chromosomal DNA indicated that the position of Tn5 seq 1 in the met gene of the donor was unaltered, and that Tn5 seq 1 did not transpose into the BCG chromosome.

Southern analysis was then carried out upon Hind III digested and XhoI digested chromosomal BCG DNA from nine additional kanamycin-resistance transformants, obtained by the transformation of linearized pYUB146, with the XhoI probe obtained from the BCG met gene. The three donor bands A, B, and C were detected in all nine clones, indicating that homologous recombination had not occurred. Because guanine and cytosine nucleotide rich mycobacterial DNA may yield very large Hind III fragments which are not resolvable by standard gel-electrophoresis, Southern blot analysis was performed by hybridizing Ava I digested chromosomal DNA of the twelve clones with a vector probe, in order to establish the randomness of the integration of band D hereinabove mentioned. As shown in FIG. 12, the probe detected four fragments in pYUB146, (lane 1), no fragments in wild type BCG (lane 2) and two internal fragments which were conserved in each clone (lanes 3–14), and fragments E and F, which varied in size and showed different patterns in each clone, indicating that integration had taken place at random sites, and thus establishing that a high degree of illegitimate recombination occurs in BCG.

EXAMPLE 4

In this example, experiments were undertaken to determine if the illegitimate, or non-homologous recombination hereinabove mentioned is a feature of BCG, or of the methionine (met) gene.

Figure 14:
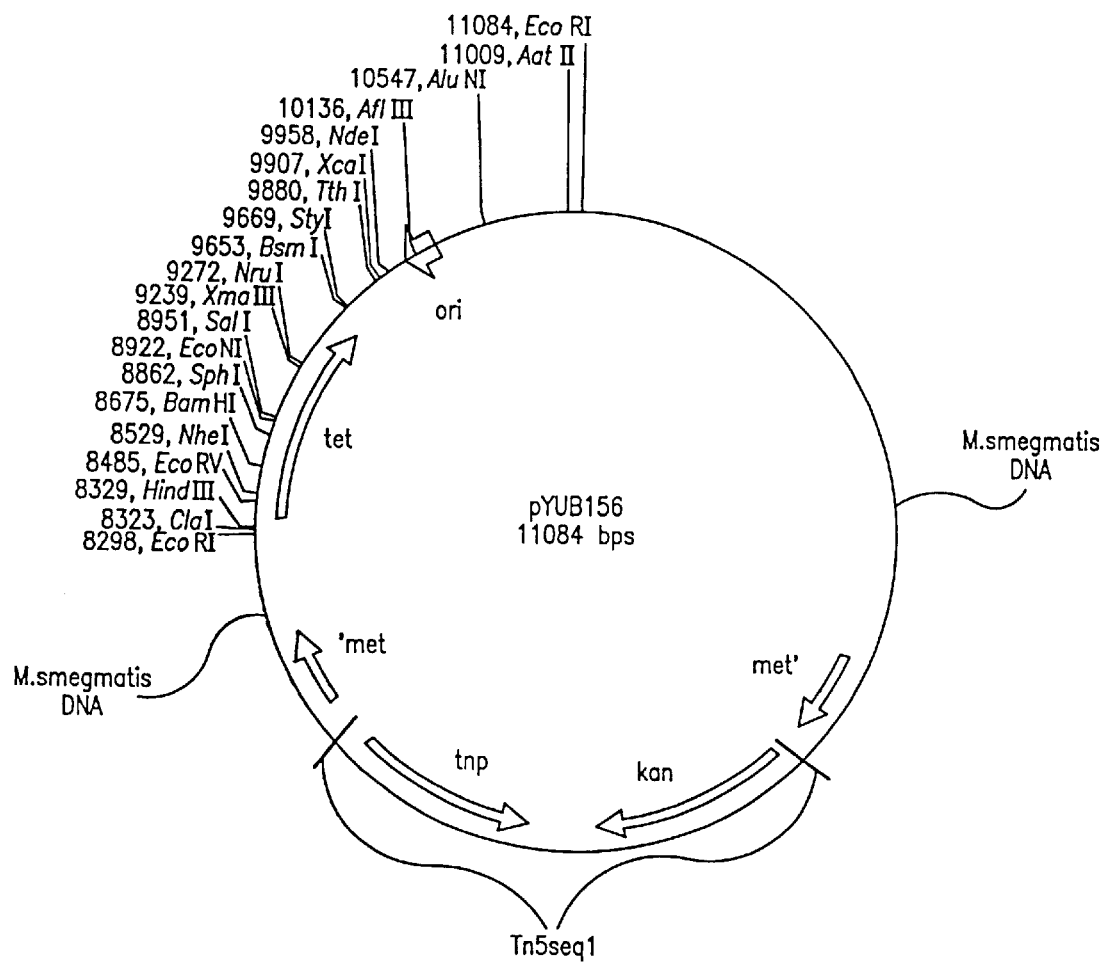
FIG. 14. Representation of plasmid pYUB156.

Tn5seq1 is inserted into pBR322 to form pYUB244 (FIG. 13). Equal quantities of circular and linearized pYUB244 were electroporated into *M. smegmatis*. Such electroporation resulted in no integration of either circular or linear pYUB244. Integration was determined by selection for kanamycin resistance (Snapper, et al., (1988)), followed by Southern blot analysis. Equal quantities of circular and linearized pYUB156 (FIG. 14), which has Tn5seq1 inserted in the complementing met clone of *M. smegmatis*, were then electroporated into *M. smegmatis*. The frequency of kanamycin-resistant colonies using both linear or circular pYUB156 was about equal, as determined by the procedure of *Snapper*, et al. (1988) followed by Southern blot analysis. Southern blot analysis of six of the kanamycin-resistant colonies of *M. smegmatis* indicated that integration of pYUB156 occurred at the Eco RI fragment of the chromosome in all six colonies. Such results indicate that mycobacterial homologous sequences are required for integration into the *M. smegmatis* chromosome, and that integration in *M. smegmatis* occurs through homologous recombination.

Equal quantities of circular and Eco RI digested pYUB244 and Tn5seq1 inactivated BCG met clones (pYUB146; pYUB147, and pYUB149) were electroporated into BCG. Linear fragments but not circular plasmids, of the above integrated into the chromosome at a frequency of about $10^{-6}$ to about $10^{-4}$/ug of DNA, irrespective of whether such fragments contained mycobacterial DNA. Integration is determined by two criteria: (1) that colonies are kanamycin-resistant; and (2) that chromosomal DNA from transformants hybridized with the donor molecule as evidenced by Southern blot analysis as hereinabove described.

Figure 15:
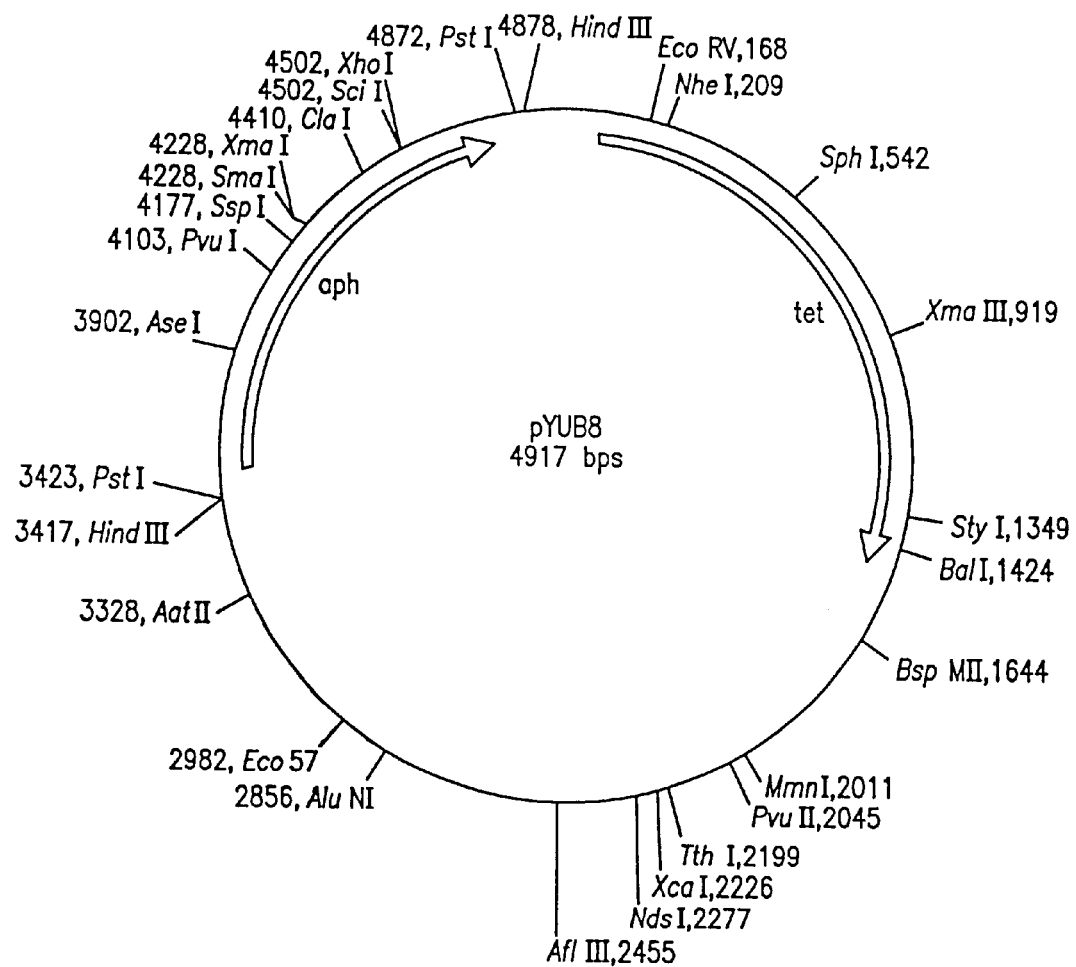
FIG. 15. Representation of plasmid pYUB8.

A further experiment was then carried out in which BCG was electroporated with circular and linear pYUB244 and pYUB8 (FIG. 15). pYUB8 is a pBR322 derivative is which the amp gene of pBR322 is replaced with the aph (kamamycin resistance) gene of Tn893 (Snapper, 1988), and which lacks sequences from Tn5seq1. In this experiment, circular DNA of both pYUB244 and pYUB8 gave only 1 transformant per ug DNA, whereas linearized and pYUB8 gave 12 and 10 transformants per ug DNA, respectively, according to the procedure of *Snapper*, et al. (1988), followed by Southern blot analysis. These results indicate that the illegitimate recombination in BCG is not dependent upon the transposase function of Tn5seq1.

EXAMPLE 5

In this example, equal quantities of circular and linear pYUB244 and pYUB147 were electroporated into the virulent H37Rv strain of *M. tuberculosis* (obtained from Dr. Wilbur Jones, Centers for Disease Control, Atlanta, Ga.) The results of such electroporation indicated that the linear forms of both pYUB147 and pYUB244 integrated at a higher frequency into the *M. tuberculosis* chromosome, as determined by *Snapper*, et al. (1988), followed by Southern blot analysis. The above results indicate that illegitimate recombination is not restricted to BCG.

EXAMPLE 6

Isolation and Characterization of BCG Isoleucine-Leucine-Valine Auxotrophs Using Illegitimate Recombination BCG-Pasteur was transformed via electroporation with linearized pYUB244. Following electroporation, the BCG cells were plated on Middlebrook 7H10 agar containing 0.5 mg/ml casamino acids and 20 μg/ml kanamycin. Kanamycin-resistant colonies were screened for their ability to grow on Sauton minimal agar, and were screen for auxotrophy as described in Davis, et al. (1980). Auxanography analysis revealed that one BCG mutant, designated mc$^2$716, required isoleucine, leucine, and valine to grow.

Figure 16:
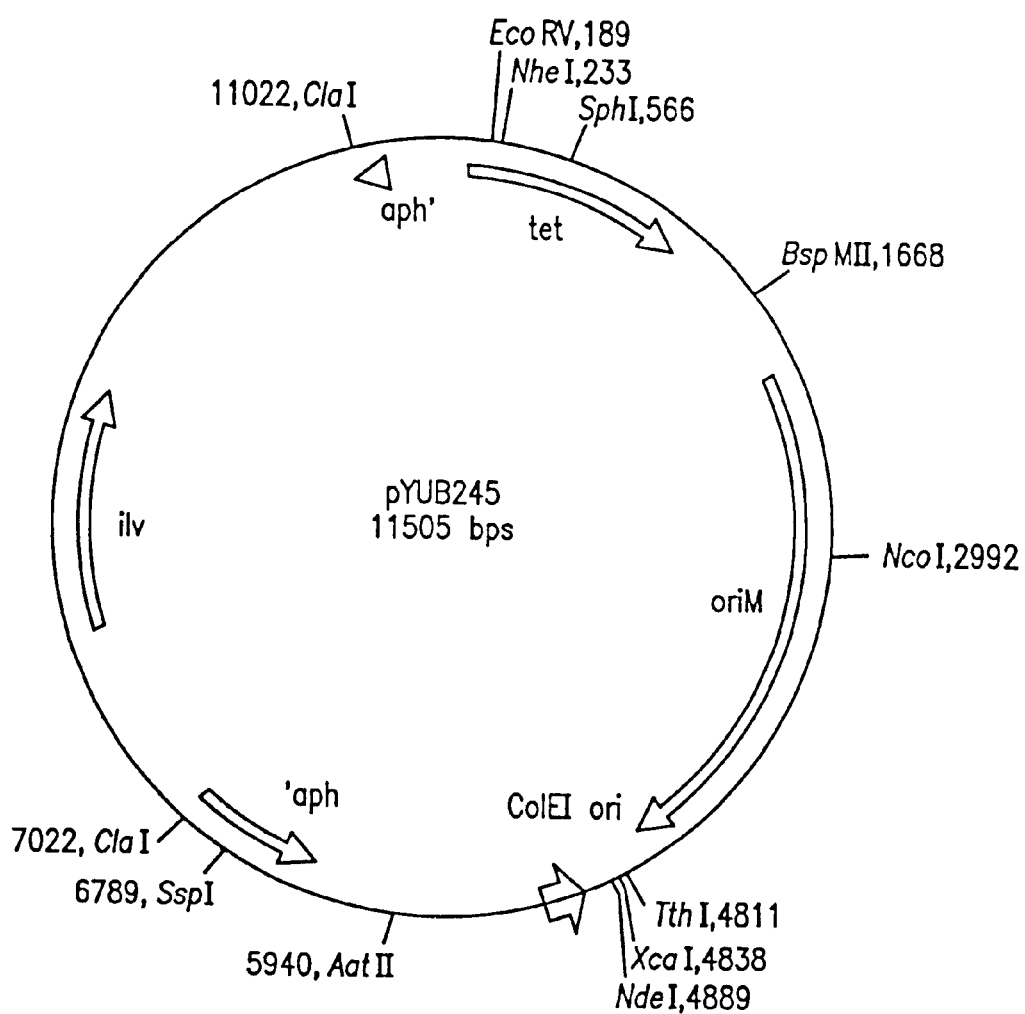
FIG. 16. Representation of plasmid pYUB245.

A genomic library of BCG Pasteur was constructed by ligating 4 kb–7 kb Msp-I digested chromosomal fragments to Cla I-digested pYUB53 (FIG. 3), as hereinabove described in Example 2. Ligated DNA's were then introduced into *E. coli* strain ec$^2$270, and plasmids were isolated from the pool of *E. coli* as described in Snapper, et al. (1988), and were electroporated into BCG strain mc$^2$716, deposited on ATCC No. 55203. A plasmid which conferred prototrophy to mc$^2$716 (referred to as an isoleucine-leucine-valine complementing clone), and which contains the BCG ilv gene, was isolated as described in Snapper, et al. (1988). This plasmid is referred to as pYUB245 (FIG. 16).

EXAMPLE 7

A. Construction of Plasmid Containing Mutated asd Gene of *M. smegmatis*

Figure 17:
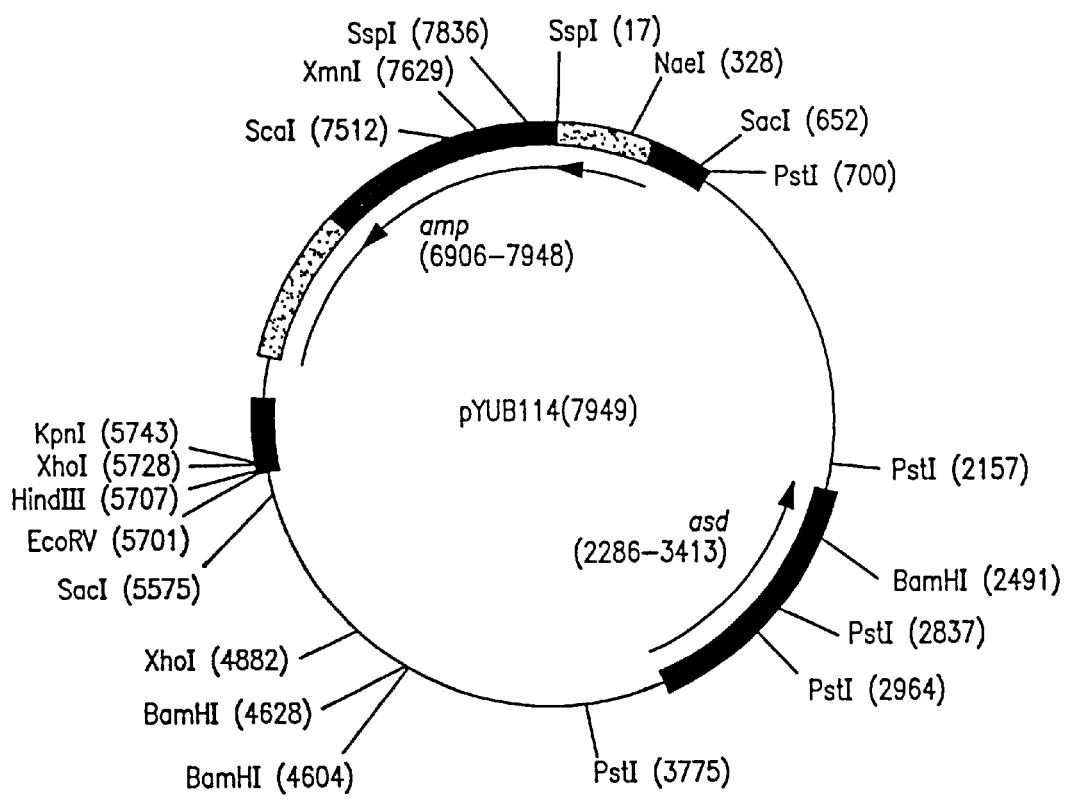
FIG. 17. Representation of plasmid pYUB114.
Figure 18:
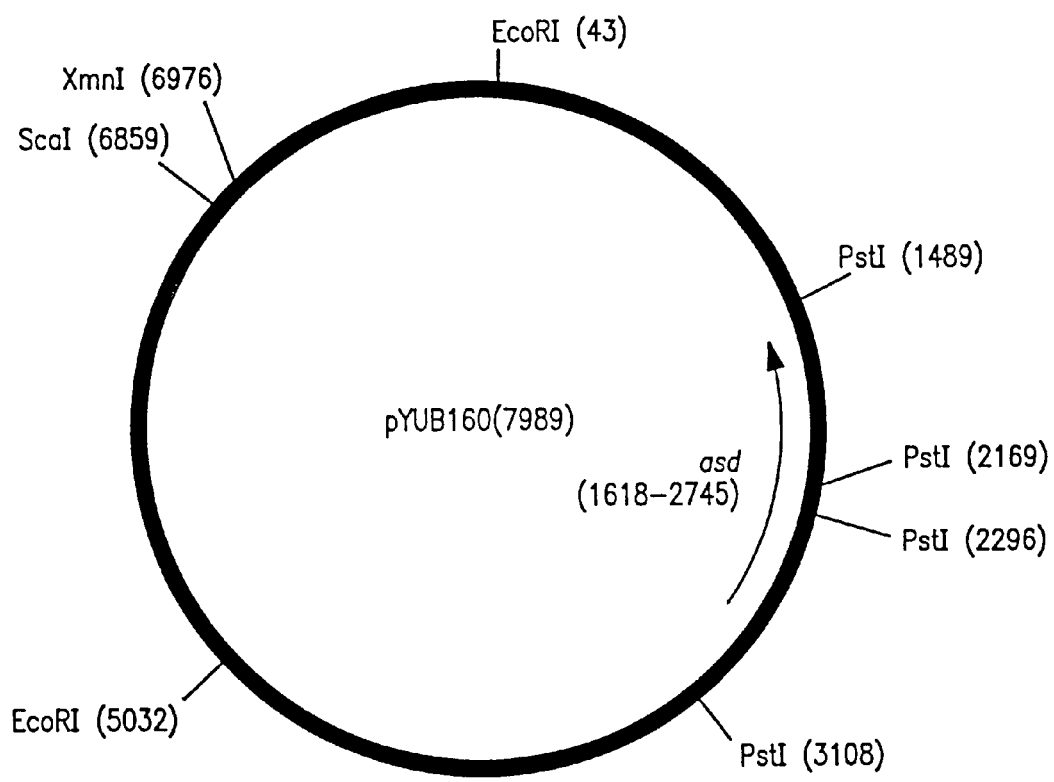
FIG. 18. Representation of plasmid pYUB160.

The aspartate semialdehyde dehydrogenase (asd) gene encodes an enzyme that catalyzes an early step in the biosynthesis of diaminopimelic acid (DAP) from aspartate, and thus is a critical component in the cell wall biosynthesis of mycobacteria. A strain containing a mutation in the asd gene and its complementation by the asd gene on a recombinant DNA vector would represent a useful auxotrophic selection system for maintenance of vectors in vivo. The *M. smegmatis* asd gene was cloned by complementing an asd mutant of *E. coli* and determining the nucleic acid sequence according to the procedure of Jacobs, et al., *PNAS*, Vol. 83, pgs. 1926–1930 (1986). The asd gene is carried on a 5 kb EcoRI fragment that has two PstI sites in the middle of the gene and two PstI sites flanking the gene. The asd gene was cloned into the EcoRI site of p Bluescript KS+(Stratagene, La Jolla, Calif.), and the resulting plasmid was designated pYUB114. (FIG. 17). pYUB114 was digested with EcoRI, the large EcoRI fragment was then isolated and ligated to pGEM7Zf+ (Promega) at the EcoRI site to form pYUB160 (FIG. 18). pYUB160 was cut with PstI, and a large fragment having a deletion of the central 1,637 bp of the asd gene was isolated. pYUB8 (FIG. 15) was cut with PstI, a PstI kan$^R$ cassette was isolated from pYUB8 and ligated to the large PstI fragment from pYUB160.

Figure 19:
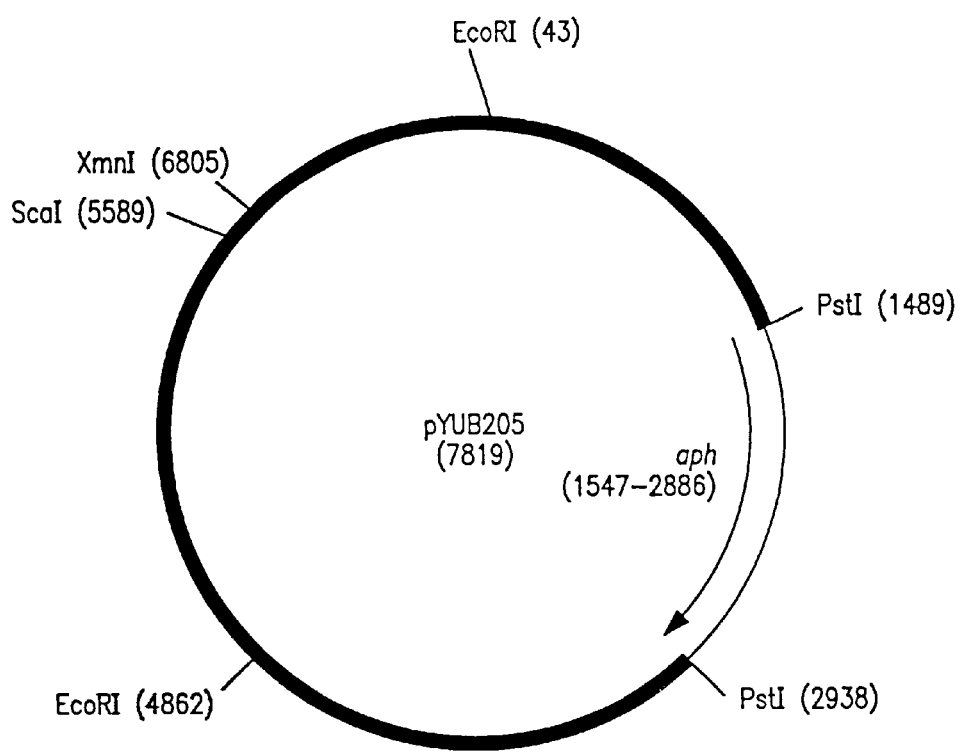
FIG. 19. Representation of plasmid pYUB205.
Figure 20:
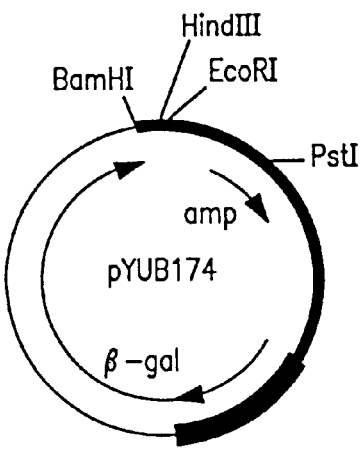
FIG. 20. Representation of plasmid pYUB174.
Figure 21:
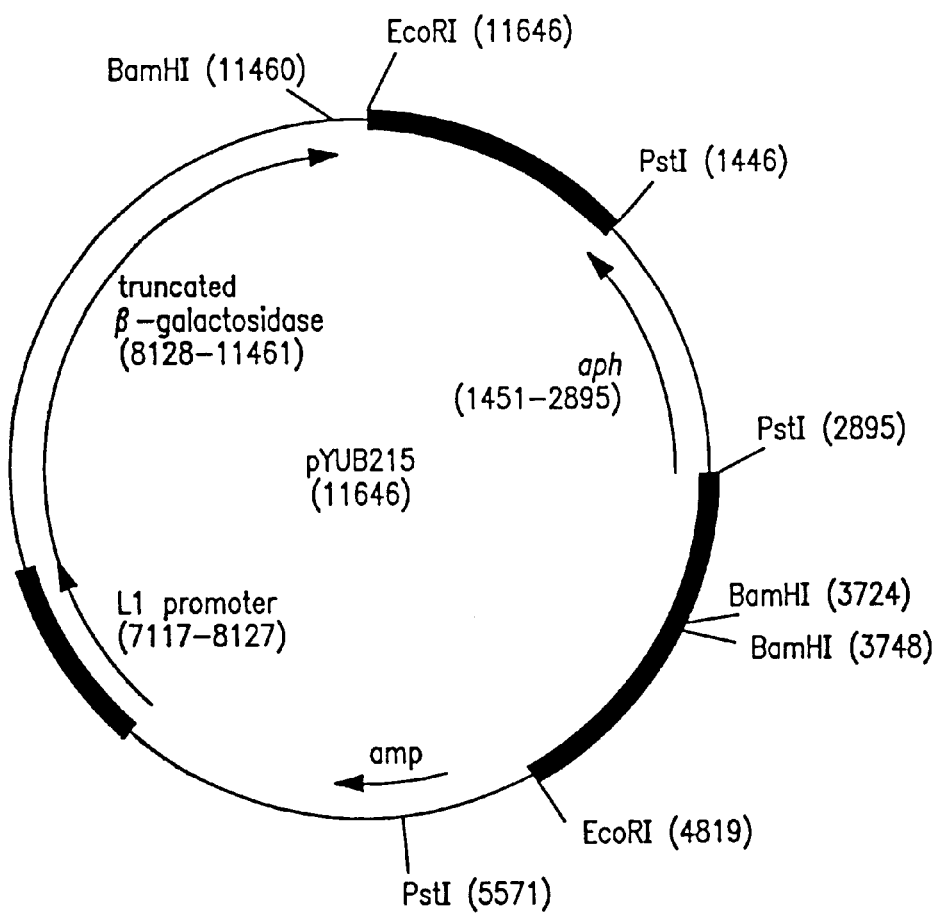
FIG. 21. Representation of plasmid pYUB215.
Figure 22:
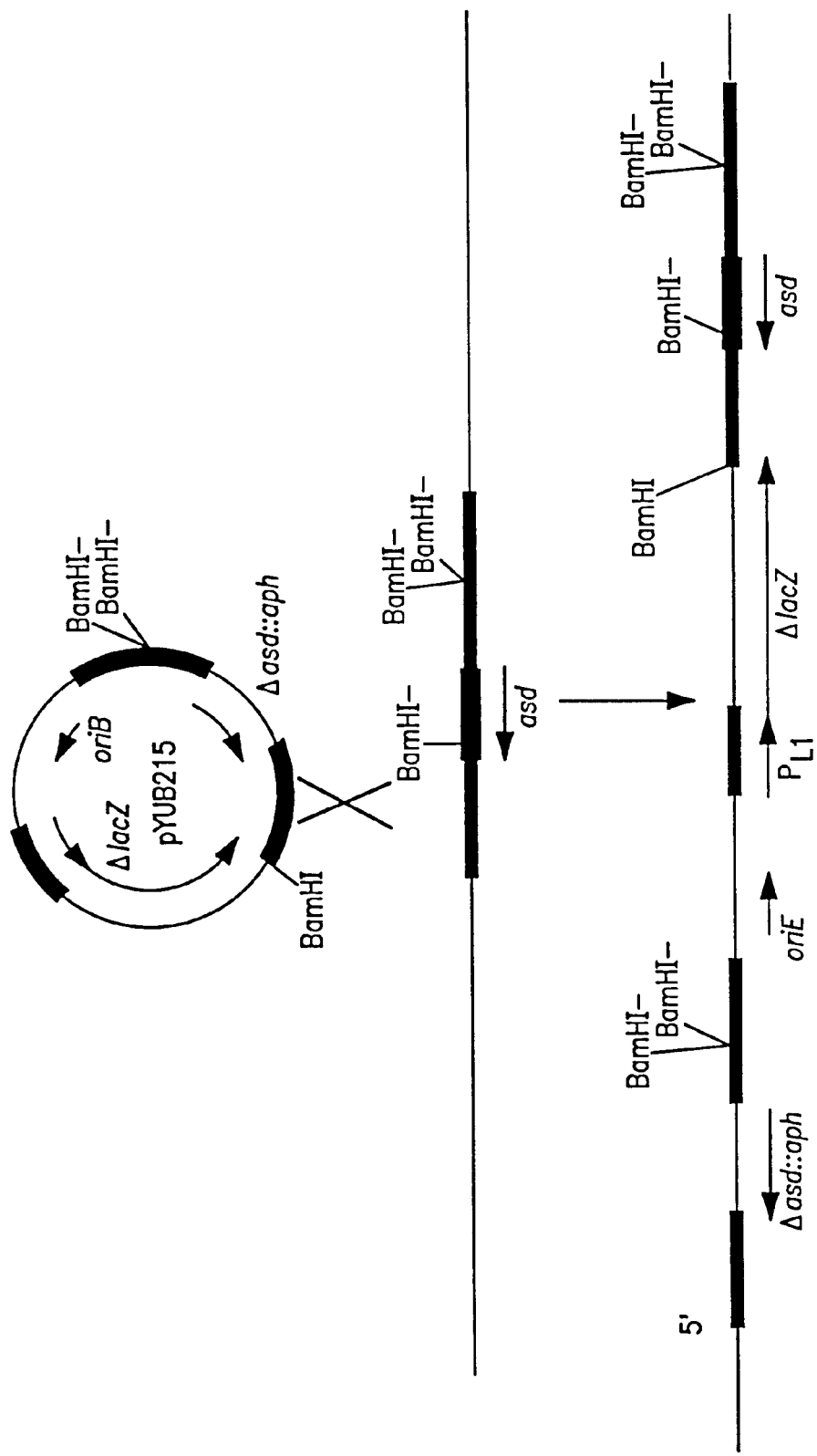
FIG. 22. Crossover recombination between pYUB215 and *M. smegmattis* chromosome. Described in Example 7.

The resulting ligation was transformed into *E. coli* strain DH5α selecting for ampicillin resistance carried on pYUB114 by electroporation. (Dower, et al., *Nucl. Acids Res.*, Vol. 16, pgs. 6127=14 6145). Transformants were screened for replacement of the central 1,637 bp of the asd gene with the 1.3 kb kan$^R$ cassette. The resulting plasmid, pYUB205 (FIG. 19), has a 1,637 bp deletion of the asd gene which is replaced by the aph gene, such deletion and replacement sometimes hereinafter referred to as Δasd::aph. pYUB205 then was cut with EcoRI and the large fragment isolated from an agarose gel. The fragment was then ligated to pYUB174 (FIG. 20) which had been cut with EcoRI and phosphatased with calf intestinal phosphatase (Boehringer Mannheim, Indianapolis, Ind.). The plasmid pYUB174, which contains the β-galactosidase gene was constructed by placing the previously isolated mycobacteriophage L1 promoter (Barletta, et al., *J. Gen. Microbiol.*, Vol. ___, pgs. ___ (1991)) upstream of a truncated β-galactosidase gene, to allow expression of β-galactosidase in mycobacteria. The resulting plasmid, pYUB215 (FIG. 21), contains the Δasd::aph gene and a truncated β-galactosidase gene controlled by a mycobacteriophage L1 promoter.

B. Construction of mc²687 pYUB215 was transformed by electroporation into *M. smegmatis* strain mc²6 according to the procedure of Jacobs, et al., *Meth. Enzymol.*, Vol. 204, pgs. 537–555 (1991). This transformation was then plated out on M-ADC plates with 15 g/l bacto-agar (Jacobs, et al., 1991), and containing kanamycin, added at 10 μg/ml and 5-bromo-4-chloro-3-indolyl- -D-galactoside (X-gal), added at 80 μg/ml, such medium also sometimes hereinafter referred to as M-ADC-KX. The plates were incubated at 37° C. until colonies were visible. Blue colonies were picked and screened by Southern blot analysis to establish integration of pYUB215.

Figure 23:
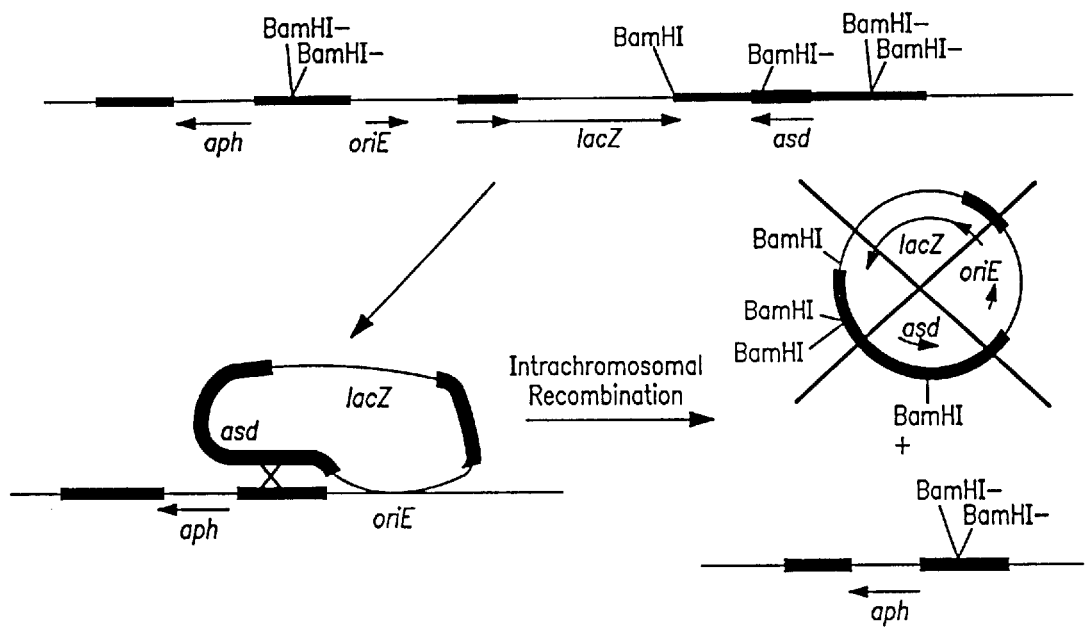
FIG. 23. Crossover recombination for Δasd::aph. Described in Example 7.

When the plasmid pYUB215 was initially transformed into *M. smegmatis*, blue and kanamycin resistant colonies were obtained at a frequency of $10^{-5}$ to $10^{-6}$ colonies per microgram of DNA, as compared to a transformation efficiency control vector pMV261 (Stover, et al., *Nature*, Vol. 351, pgs. 456-460 (1991)), on M-ADC-KX agar containing DAP and casamino acids. No significant numbers of white colonies were obtained above a background of 1 to 5 colonies. The blue colonies were inferred to be generated by a single crossover recombination event between pYUB215 and the *M. smegmatis* chromosome. The single crossover event likely occurred between the *M. smegmatis* DNA sequences that flank the aph gene that are identical to the *M. smegmatis* DNA sequences that flank the asd gene in the *M. smegmatis* chromosome. Southern analysis of 8 independent transformants confirmed that pYUB215 had integrated on either side of the aph gene, and one such transformant was designated strain mc²687. The inability to generate replacements of the chromosomal asd gene with the mutant Δasd::aph allele is interpreted as indicating that the asd gene is essential or that double crossover events occur at an extremely low frequency in mycobacteria. The necessity of having simultaneous double crossover events can be observed by constructing the chromosomal Δasd::aph mutant in a two-step process. Because mc²687 has already undergone a single crossover event to integrate pYUB215, a second recombination event between homologous sequences of the two alleles in the chromosome may produce the desired mutant. In the second recombination event, shown in FIG. 23, the 3' end of the asd gene aligns itself with the 3' end of the Δasd::aph gene. These two "3' end" sequences are homologous. Through intrachromosomal recombination, a circular plasmid, which contains the asd gene, the lac Z gene, and an *E. coli* origin of replication (ori E) should be looped out of the chromosome. Thus it should be possible to screen for intrachromosomal recombination by the loss of B-galactosidase when the plasmid sequences are looped out during this event because the plasmid does not include a mycobacterial origin of replication.

C. Isolation of β-galactosidase Mutants of mc²687

Strain mc²687 was grown up in M-ADC-TW medium and kanamycin, and aliquots were plated out on M-ADC agar with the addition of kanamycin and X-gal and screened for the production of white colonies.

Figure 24:
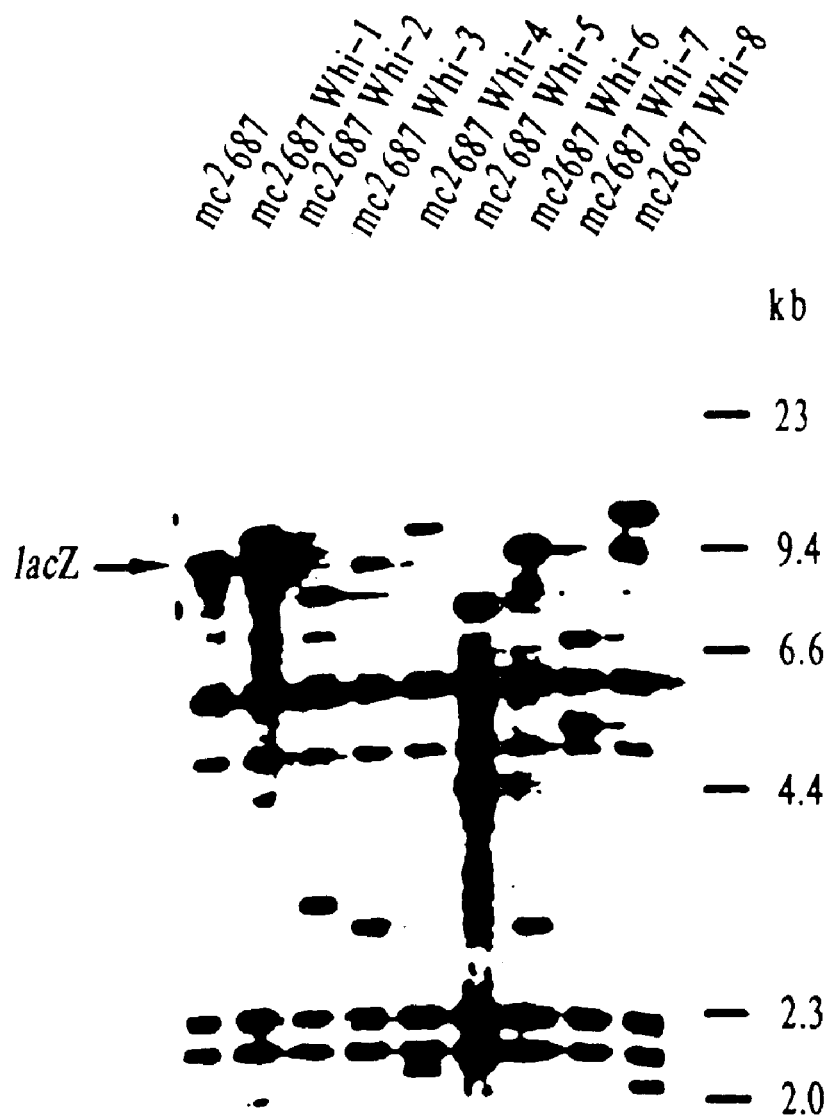
FIG. 24. Southern blot analysis of mc²687 and 8 white mutants of mc²687 having lost β-galactosidase activity. DNA probed with pYUB215. Described in Example 7.

White mutants of mc²687, having lost β-galactosidase activity, were obtained at a frequency of $8 \times 10^{-5}$ per cell. Southern analysis of BamHI digests of total chromosomal DNA from 8 clones compared to mc²687 is shown in FIG. 24. The DNA was probed with pYUB215. As shown in FIG. 24, from the top of the blot, in the mc²687 lane the second and fifth bands are flanking BamHI fragments to the integrated pYUB215 and the first, third, and fourth bands correspond to internal fragments from pYUB215 (first) or the chromosomal asd gene (third and fourth bands). As shown by the arrow, the lacZ gene (β-galactosidase gene) fragment is the largest band, at about 9.5 kb. All white mutants show a shift in the size of the lacZ band and an extra smaller band. The size of the smaller band added to the lacZ band results in a fragment of about 11.5 kb in length, which can be explained by insertion of an approximately 2.2 kb insertional element (IS-element), or transposon, which contains a BamHI site, into the lacZ gene.

Figure 25:
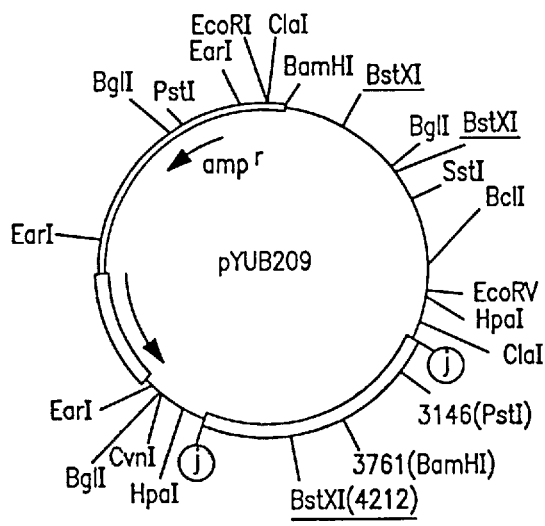
FIG. 25. Representation of plasmid pYUB209.

The insertion element which is inserted in the galactosidase gene can be recovered by cutting total chromosomal DNA isolated from a clone containing the insertional element with EcoRI to completion. EcoRI digestion will free a fully functional *E. coli* plasmid because the Δasd::aph gene was cloned into pYUB174 at the EcoRI site. Digestion with EcoRI will free the original pYUB174 plasmid which now contains a copy of the insertion element. To isolate the insertion element, EcoRI digested DNA was self-ligated at a DNA concentration of less than 5 ng/μl and transformed into the *E. coli* strain DH5 selecting for ampicillin resistance encoded by the β-lactamase gene carried on pYUB174. One clone containing the insertional element, designated as IS1096, was designated as pYUB209 (FIG. 25).

D. Characterization of IS1096

Figure 26:
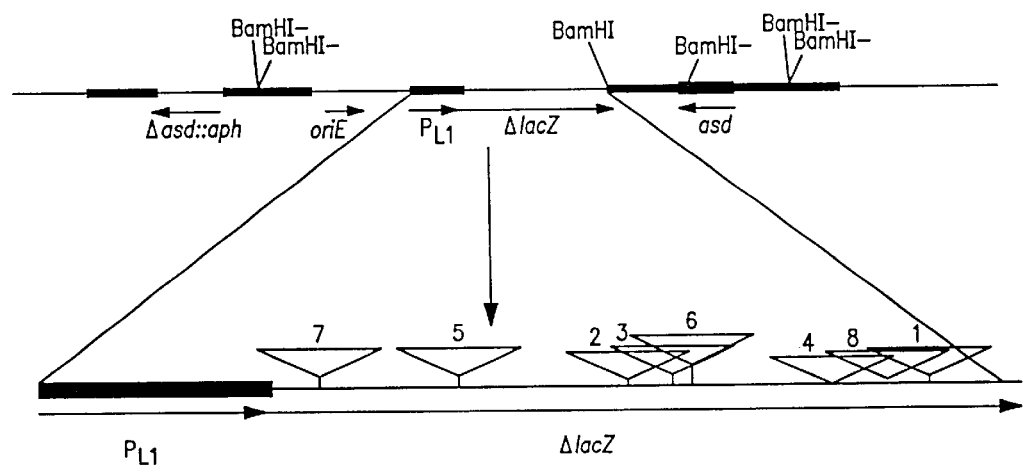
FIG. 26. Representation of the approximate positions of eight insertions of IS1096 into the pYUB215 β-galactosidase gene.

The approximate positions of eight insertions of IS1096 into the β-galactosidase gene are shown in FIG. 26. The approximately positions of the eight IS1096 transpositions into the pYUB215 β-galactosidase gene were determined by Southern analysis. Restriction mapping of IS1096 gave the orientation of the BamHI site within the insertion element to allow accurate approximation of the positions of the insertions into the lacZ gene. From the distribution of insertions in the β-galactosidase gene, IS1096 transposes in a random fashion.

In order to determine more accurately the frequency of IS1096 transpositions in *M. smegmatis,* 10 individual colonies of mc²687 were grown to stationary phase in 5 ml M-ADC-TW with kanamycin until saturation. Dilutions of these 10 independent cultures were plated out on M-ADC-KX plates such that approximately 1,000 colonies per plate were obtained. The cells from each culture were then plated on 20 M-ADC-KX plates to screen for white colonies. The number of white colonies divided by the total number of colonies present represents the frequency of isolation of mutations in the β-galactosidase gene of mc²687. The average frequency of loss of β-galactosidase activity in these cultures was $7.2 \times 10^{-5}$ per cell. This number includes only those colonies which proved to be truly negative for β-activity when secondarily screened on X-gal containing plates.

E. Restriction Analysis of IS1096

IS1096 in pYUB209 was located within the β-galactosidase gene between two HpaI sites. To facilitate sequencing of the insertion element, this HpaI fragment was cloned in both orientations into the SmaI site of pGEM7Zf+ (Promega). Once this fragment was cloned into pGEM7Zf+, several deletions were constructed using opportune sites in IS1096 and the polylinker of IS1096. Deletions were made from BstXI and BamHI sites within IS1096 in both directions into the polylinker of pGEM7Zf+. Having these deletions allowed sequencing in both directions from these sites into IS1096. Sequencing of both strands of IS1096 and the junction between IS1096 and pYUB209 was done using synthetic oligonucleotides as well. Sequencing reactions were carried out using Sequenase Version 2.0 (United States Biochemical Corp.) on double stranded DNA templates, as described in Kraft, et al., Bio Techniques, Vol. 6, pgs. 544–547 (1988).

Figure 27:
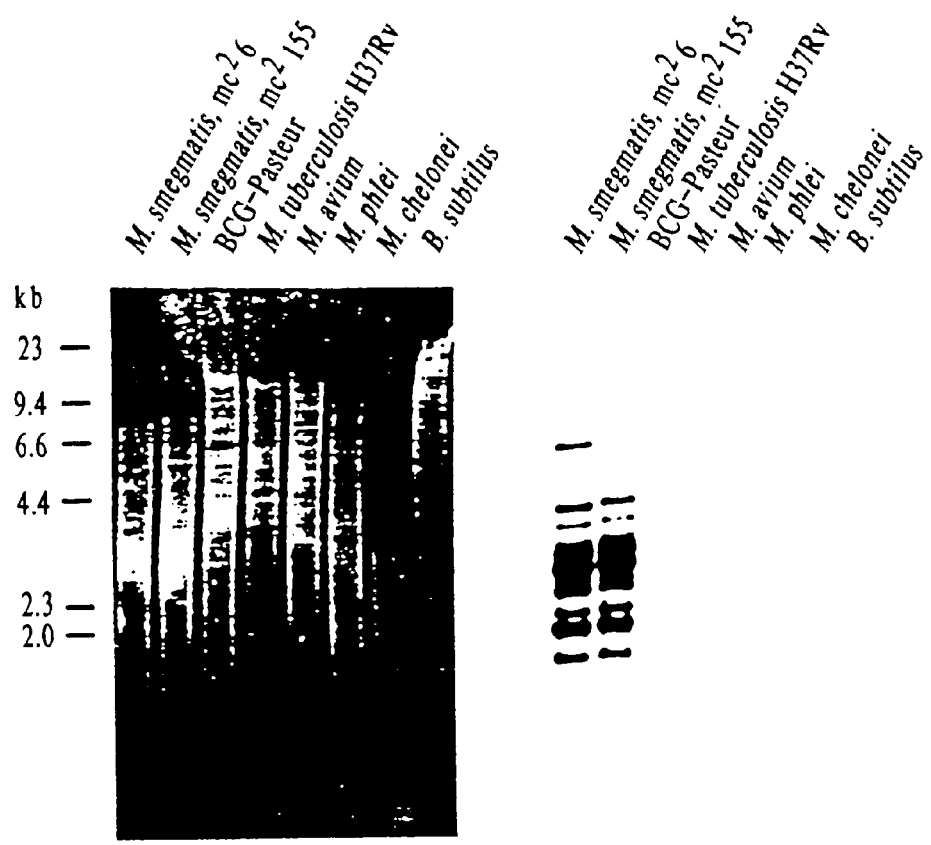
FIG. 27. Southern analysis of *M. smegmatis* and other mycobacteria using the internal IS1096 fragment as a probe. Described in Example 7.

Southern analysis of Streptomyces coelicolor, E. coli strain K-12, Bacillus subtilus, and 12 species of mycobacteria was performed using the internal IS1096 fragment, shown as a solid bar between the BamHI and BstXI sites shown as a graphic representation in FIG. 29, as a probe. As shown in FIG. 27, IS1096 is present only in M. smegmatis. The pathogenic strains of mycobacteria, M. tuberculosis, M. bovis, M. avium, and M. leprae, lack the insertion element.

Figure 28:
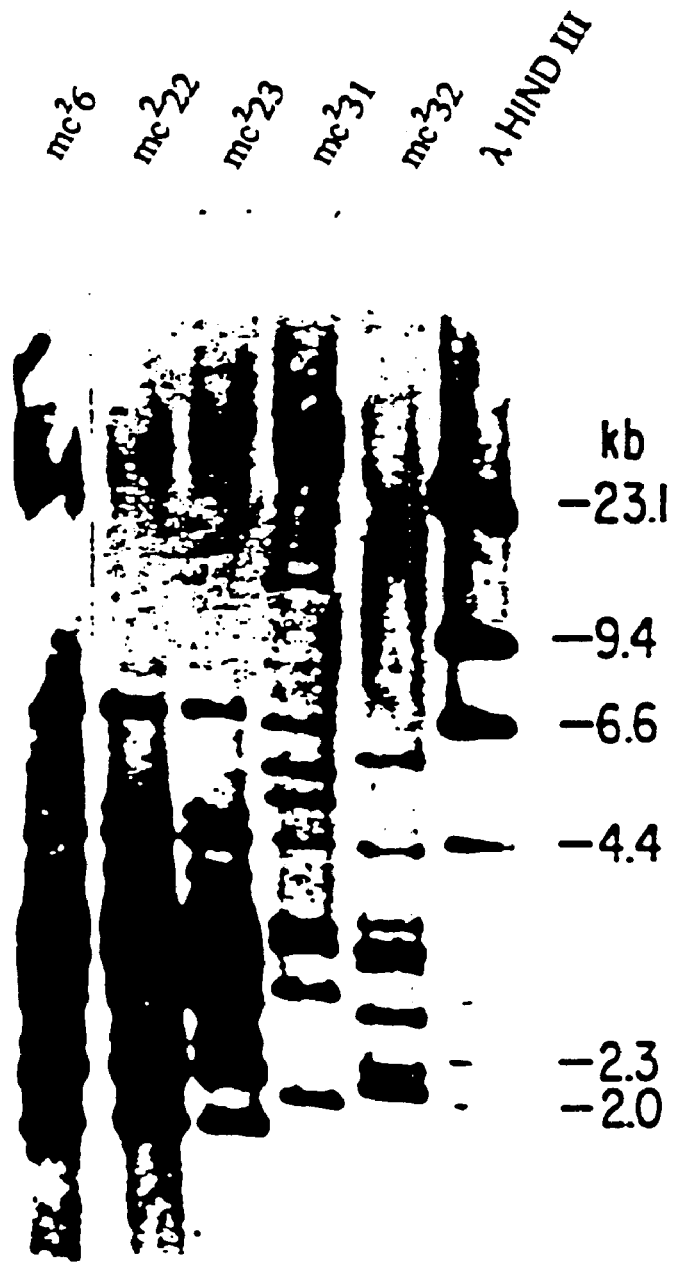
FIG. 28. RFLP analysis of IS1096 in different *M. smegmatis* isolates. Described in Example 7.

Several different M. smegmatis isolates, including the three morphotypes of M. smegmatis, strain ATCC607, were probed by Southern analysis to determine the degree of variation in restriction pattern when probed with IS1096. Southern analysis was performed with IS1096 upon PstI digests of total chromosomal DNA isolated from M. smegmatis $mc^26$, $mc^222$, $mc^223$, $mc^231$, $mc^232$, and DNA cut with HindIII (size standard radioactively labeled). The blot is shown in FIG. 28. Lane 1 is $mc^26$, lane 2 is $mc^222$, lane 3 is $mc^223$, lane 4 is $mc^231$, lane 5 is $mc^232$, and lane 6 is DNA cut with HindIII size standard radioactively labeled. As shown in FIG. 29, there is considerable variability in the different isolates. Only one band appears in all of the isolates, and the number of insertional elements found ranges from 8 to 16. Both $mc^222$ and $mc^223$ were found to have an additional copy of IS1096 not present in $mc^26$.

F. Nucleotide Sequence of IS1096

The sequence of IS1096 is shown in FIG. 29. Sequence analysis, carried out as hereinabove described, revealed that IS1096 is 2275 bp in length, and the percentage of guanine and cytosine (G+C) is 67%, which is equal to that normally observed in the M. smegmatis chromosome. (Wayne, et al., J. Bacteriol., Vol. 96, pgs. 1915–1919 (1968)). The internal regions of IS1096 have areas of higher G+C ranging from about 70% to about 80%, as well as areas similar to the average G+C content; however, the G+C content of the ends of the insertional element have a G+C content of less than 60%.

A well conserved inverted repeat sequence is observed at both ends of IS1096, which is 25 bp in length, is indicated in bold type in FIG. 29. Two mismatches are present in the inverted repeats. Transposition into the β-galactosidase gene resulted in a duplication of 8 bp, indicated by underlined bold type, of target DNA sequences on both sides of the insertion point. This duplication is consistent with the mechanism of transposition of most insertion elements. Three sets of inverted repeats of approximately 9 bp in length were found in the 3' end of IS1096, the positions of which are shown in FIG. 29, as designated by pairs of arrows in opposite orientation.

Open reading frame (ORF) analysis of the sequence of IS1096 revealed the presence of 13 ORF's which are longer than 100 amino acids. None of the putative ORF's displayed high levels of homology to proteins encoded by other insertion elements; however, two of the ORF's are distantly related to previously sequenced tnp A transposase and tnp R genes, as described in Turner, et al., Nucl. Acids Research, Vol. 17, pg. 1757 (1989) and in Rowland, et al., Mol. Microbiol., Vol. 4, pgs. 961–975 (1990), as shown in FIG. 29. A large 414 amino acid ORF with a valine initation codon was found which is a transposase, and which has 21.1% identical and 66% homologous amino acids over 185 amino acids with the transposase from Tn 3926 (Turner, et al., (1989)). The transposase of IS1096 is indicated in FIG. 29 as tnpA and is sometimes herein referenced to ORFA. A 237 amino acid open reading frame which also begins with a valine is in the opposite direction to the tnp A gene as shown in FIG. 29 and is designated as tnp R. The amino terminal 92 amino acids of tnp R are 18.5% identical and 69% homologous to the amino terminus of the Tn1000 resolvase. tnpR is sometimes herein referred to as ORFR. (Reed, et al., Nature, Vol. 300, pgs. 381–383 (1982)). The proteins encoded by these ORF's are of a similar size and significantly more similar than the other ORF's found on IS1096 to standard transposase and resolvase proteins.

EXAMPLE 8

IS1096 is cloned out of M. smegmatis, and a construct is made in which a sequence encoding the transposase(s) was removed from IS1096 and replaced with an aph gene (which was hereinabove described). The sequence encoding the transposase(s) remains in the resulting construct but is located outside of the inverted repeat sequences. The resulting construct is then cloned into pGEM7Zf+. The resulting plasmid is then transformed into M. bovis-BCG, and M. bovis-BCG cells are plated out on complete nutrient medium containing kanamycin and selected for kanamycin resistance. Surviving colonies are those

TABLE 1

| Strain, plasmid, or transposable element | Relevant characteristics |
|---|---|
| E. coil DH5α (Bethesda Research Laboratories) | F Φ80dlacZΔM15 endA1 recA1 hsdR17 ginV thi-1 λ gyrA96 relA1 Δ(lacZYA-argF)U169 |
| M. bovis BCG | Pasteur strain |
| mc²789 | M. bovis BCG[chr::Tn5367] met |
| mc²797 | M. bovis BCG[chr::Tn5367] leu-1 |
| mc²798 | M. bovis BCG[chr::Tn5366] leu-2 |
| mc²826 | M. bovis BCG#12[chr::Tn5367] |
| mc²827 | M. bovis BCG#13[chr::Tn5367] |
| mc²828 | M. bovis BCG#14[chr::Tn5367] |
| mc²829 | M. bovis BCG#21[chr::Tn5368] |
| mc²830 | M. bovis BCG#22[chr::Tn5368] |
| mc²831 | M. bovis BCG#23[chr::Tn5368] |
| mc²849 | M. bovis BCG#11[chr::Tn5367] |
| mc²850 | M. bovis BCG#15[chr::Tn5367] |
| mc²851 | M. bovis BCG#16[chr::Tn5367] |
| mc²852 | M. bovis BCG#17[chr::Tn5368] |
| mc²853 | M. bovis BCG#18[chr::Tn5368] |
| mc²854 | M. bovis BCG#19[chr::Tn5368] |
| mc²855 | M. bovis BCG#20[chr::Tn5368] |
| mc²856 | M. bovis BCG#24[chr::Tn5368] |
| mc²857 | M. bovis BCG#25[chr::Tn5367] |
| mc²858 | M. bovis BCG#26[chr::Tn5367] |
| mc²859 | M. bovis BCG#27[chr::Tn5367] |
| mc²860 | M. bovis BCG#28[chr::Tn5367] |
| mc²861 | M. bovis BCG#29[chr::Tn5368] |
| Bluescript II KS+/− | pUC derivative, Amp$^r$ |
| pMV261 | contains oriE, oriM and aph genes |
| pYUB8 | pBR322 derivative containing oriE, aph and tet genes |
| pYUB53 | pYUBB derivative containing oriE, oriM, aph, and tet genes |
| pYUB285 | ΔoriM, contains oriE and tet genes and Tn5367 |
| pYUB297 | ΔoriM, contains oriE and tet genes and Tn5368 |
| pYUB305 | ΔoriM, contains oriE and tet genes and Tn5369 |
| pYUB312 | ΔoriM, contains oriE, aph and tet genes |
| IS1096 | M. smegmatis insertion sequence |
| Tn5366 | IS1096 derivative containing aph gene |
| Tn5367 | IS1096 derivative containing aph gene |
| Tn5368 | IS1096 derivative containing aph gene |
| Tn5369 | IS1096 derivative containing aph gene |

Plasmids and transformation. Plasmids used in transposition experiments and their features are indicated in Table 1 above. All plasmids have a ColE1 origin and an aminoglycoside 3'-phosphotransferase (aph) gene from Tn903 encoding kanamycin/neomycin resistance. This aph gene was PCR amplified from pKD368 (Keith Derbyshire, unpublished result) to include a trp transcriptional terminator (Christie, et al., Proc. Nat. Acad. Sci., Vol. 78, pgs. 4180–4184 (1981)) for use in transposon constructs. pYUB8 (Kalpana, et al., Proc. Nat. Acad. Sci., Vol. 88, pgs. 5433–5437 (1991)) additionally has a tet gene. pYUB53 (Kalpana, 1991) was derived from PYUB8 with the addition of the entire mycobacterial origin of replication from pAL5000 (Rauzier, et al., Gene, Vol. 71, pgs. 315–321 (1988)). pMV261 (Stover, et al., Nature, Vol. 351, pgs. 456–460 (1991)) also has a fully functional oriM, consisting of ORFs 1 and 2 from pAL5000. The remaining plasmids containing IS1096 were constructed as described in the Results section hereinbelow, using modifying and restriction enzymes with conditions described by the manufacturers and with PCR (Cetus). The DraIII deletion internal to the oriM was performed by digestion followed by T4 DNA polymerase treatment (Pharmacia). E. coli was transformed with plasmids by electroporation (Bio-Rad); or the CaCl$_2$ procedure using pretreated cells (Bethesda Research Laboratories). Plasmids were prepared from E. coli by both Birmboim/CsCl$_2$ (Maniatis, et al., 1982) and column (Quiagen) methods. M. bovis BCG cells were transformed by electroporation after washing in 10% glycerol as previously described (Jacobs, et al., 1991), after which 4 mls complete media; M-ADC-TW containing 0.5% casamino acids and 20 µg/ml tryptophan, was added, followed by incubation overnight at 30° C. and plating on Middlebrook 7H10 with glycerol, ADC, cyclohexamide; (Jacobs, et al., 1991), amino acid supplements (Curtiss, Manual of Methods for General Bacteriology, Gerhart, ed., Amer. Soc. Microbiol., pp. 243–265 (1981)) and kanamycin at 20 ug/ml. Colonies were counted after 3 weeks incubation at 37° C.

Southern blotting and hybridization. Single M. bovis BCG colonies were grown in 10 mls M-ADC-TW containing kanamycin and expanded 1:50 for preparation of DNA. Whole DNA was prepared from 50 ml cultures, by a ten fold scale up of the CTAB method (Van Soolingen, et al., J. Clin. Microbiol., Vol. 29, pgs. 2578–2586 (1991)). DNA was estimated by agarose gel electrophoresis and approximately 2 µg was digested with restriction enzyme and run on a 0.7% or 1% agarose gel at 40 V overnight. The DNA was transferred to nylon membrane (ICN), using conditions recommended. Hybridization was performed using plasmid pYUB285 as a probe labelled with [α-$^{32}$P]dCTP as previously described (Cirillo, et al., J. Bacteriol., Vol. 173, pgs. 7772–7780 (1991)). The sizes of fragments hybridizing on KpnI and BamHI Southern blots were estimated using the mobilities of standard DNA markers run on each gel.

Isolation of integrated transposons and sequence analyses. KpnI-digested fragments containing the integrated transposon were cut from an agarose gel and cloned into Bluescript II KS+ (Promega) using kanamycin selection. Outward primers based on the sequence of IS1096 were used with the Sequenase version 2.0 and the Longranger (United States Biochemical) acrylamide gel reagents. Sequences of the insertion sites were obtained for both DNA strands.

Auxotroph isolation. Colonies obtained on pYUB285 and pYUB297 transformation were picked using wooden sticks into 96-well plates containing complete medium. They were grown up and washed twice in minimal (M-ADC-TW) medium before being replicated onto agar plates with and without amino acid supplement using a 96-prong template (Dankar, Mass.). Promising candidates were further streaked from the original 96-well plate to check their auxotrophy and auxonographic analysis was performed on washed cultures as described (Kalpana, 1991).

RESULTS

Figure 30:
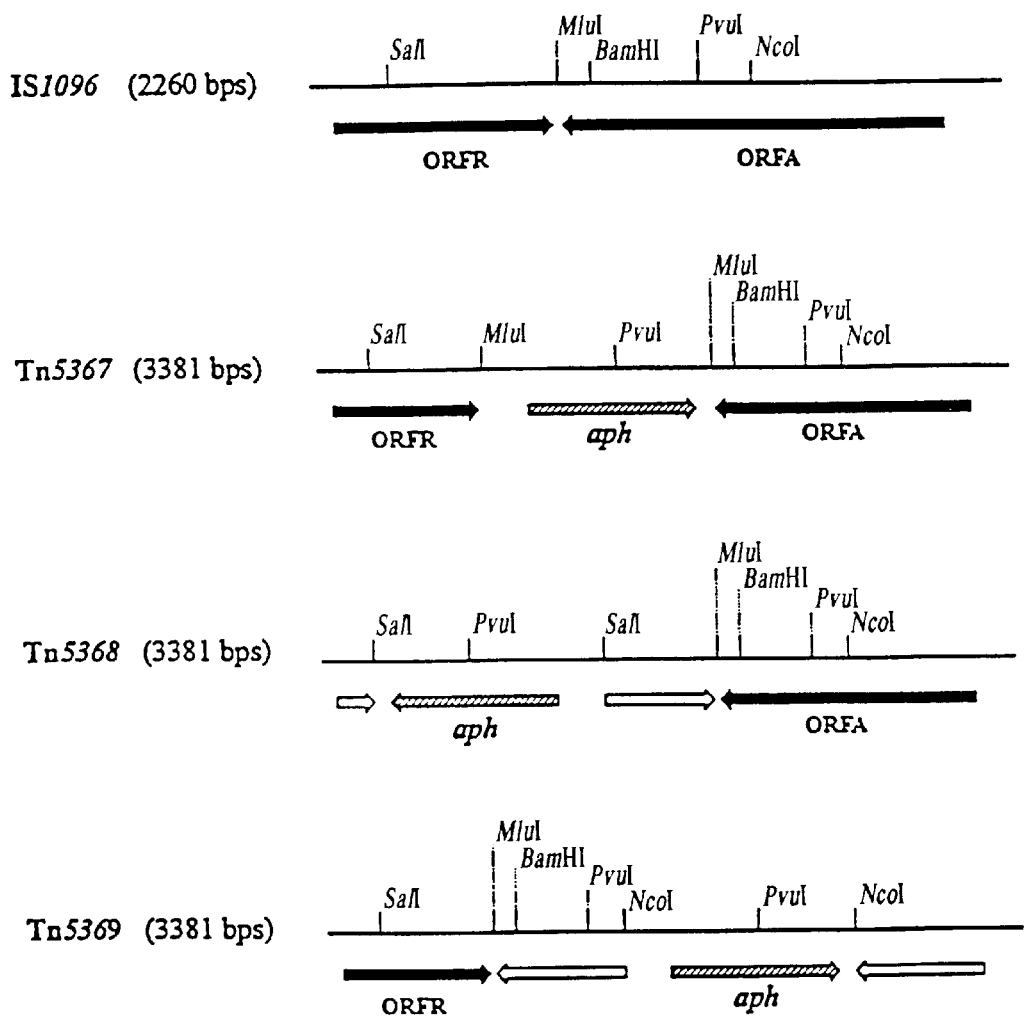
FIG. 30. Open reading frames (OFR) from IS1096, Tn5367, Tn5368, and Tn5369. Described in Example 7.

Construction of IS1096-derived transposons. The kanamycin resistance gene (aph) from Tn9O3, was PCR-amplified and cloned into the unique SAII, MluI or NcoI sites in the insertion sequence IS1096. This created a set of three transposons, having the aph gene in each of the open reading frames of IS1096, as well as between them. The elements are shown in FIG. 30. Tn5368 has the aph gene inserted into ORFR; Tn5369 has the insertion in ORFA, and in Tn5367, the aph gene does not disturb either ORF. Tn5366 is identical to Tn5367 but has the aph gene in the reverse orientation. TnpA and TnpR (Cirillo, et al., 1991) have been renamed ORFA and ORFR respectively since their function is not yet defined.

Construction of transposon delivery plasmids. IS1096, with its adjacent lacZ sequences, (100–200 base pairs on each side), had been cloned in both orientations into the multicloning site of pGEM7Zf$^+$ (Promega) (Cirillo, et al., 1991); to create plasmids pYUB234 and pYUB235, enabling excision of the element with EcoRI and HindIII. A third vector, pYUB272, was constructed, with EcoRI and HindIII sites, as well as origins of replication for *E. coli* and mycobacteria and a tetracycline resistance, or tet gene. (This plasmid was derived from pMV261 by replacement of the NotI-PstI fragment with a tetR gene obtained by PCR from pYUB53). The transposons Tn5368 and Tn5369 which were created on pYUB234 were inserted into pYUB272 by ligation after digestion with EcoRI and HindIII. Finally, in order to obtain a delivery plasmid, unable to replicate in mycobacteria, the mycobacterial origin of replication (oriM) was inactivated in each of the constructs by an internal deletion using DraIII, which removed 556 base pairs of DNA and a significant part of an open reading frame in the origin of replication (Rauzier, et al., 1988; Labidi, et al., *Plasmid*, Vol. 27, pgs. 130–140 (1992); Villar, et al., *Plasmid*, Vol.-28, pgs. 166–169 (1992).

Figure 31:
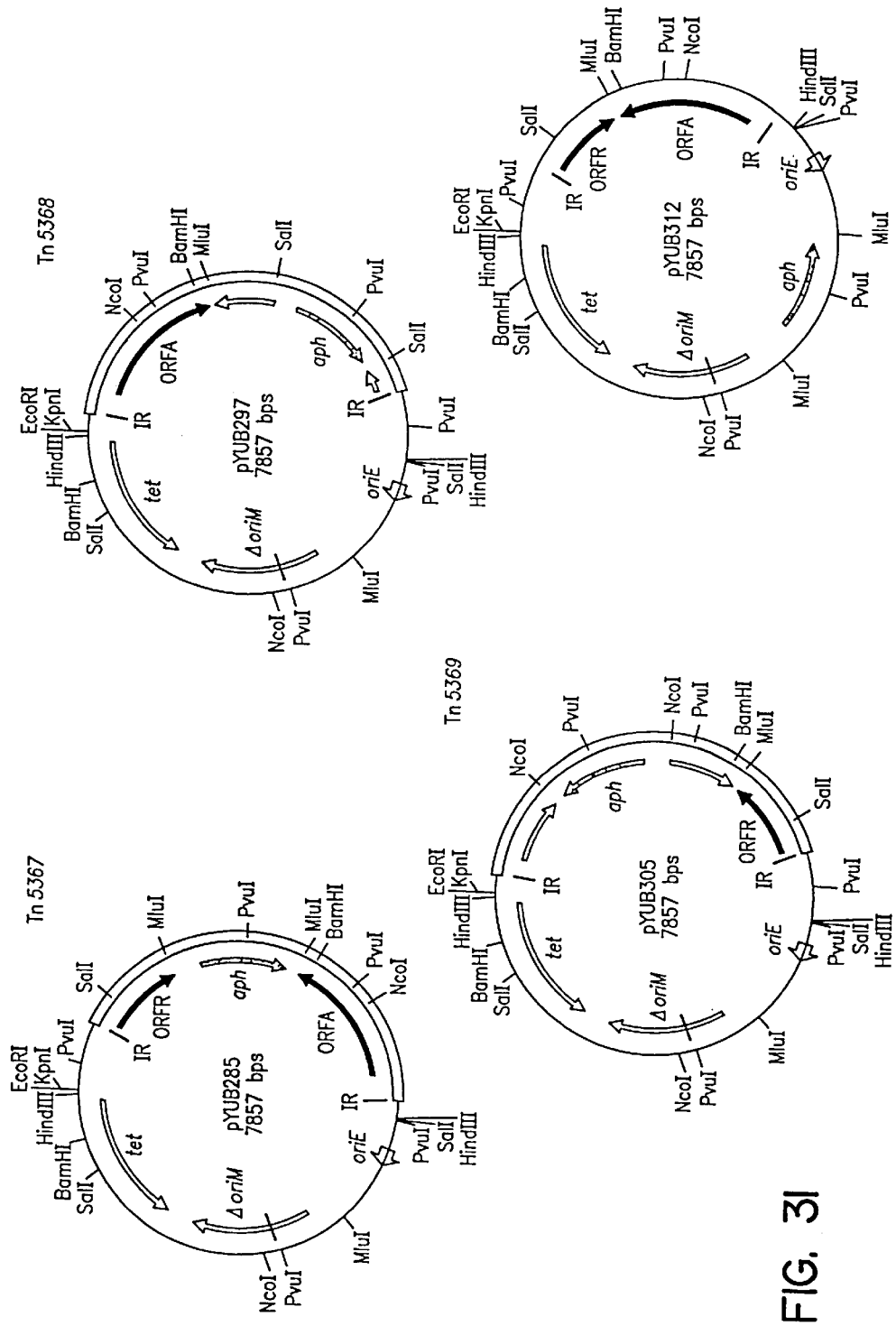
FIG. 31. Representation of plasmids pYUB285, pYUB297, pYUB305 and pYUB312.

Tn5367, having an aph gene in the MluI site, was created after, rather than before, ligation of the IS element to pYUB272. Insertion of the aph gene into the MluI site of the IS element necessitated a partial digestion since there is also an MluI site in pYUB272. The construct obtained from insertion into this second site provided a plasmid having the aph gene outside the transposon, which could then be used as a control to monitor any illegitimate integration of the plasmids (Kalpana, et al., 1991). DraIII deletions within the oriM were also performed on these two plasmids. The four plasmid delivery constructs, pYUB285, pYUB297, pYUB305 and pYUB312, are shown in FIG. 31.

Transformation of *M. bovis*-BCG with Transposon Delivery Constructs.

The numbers of kanamycin-resistant colonies resulting from five transformation experiments are shown in Table 2 below. In addition to the transposon delivery plasmids, three additional plasmids were used as controls. The efficiency of transformation was determined with an oriM-containing vector; either pMV261, or pYUB53, and any illegitimate integration was monitored using either one of two plasmids; pYUB312, with the oriM deletion, but the aph gene is outside the insertion element; or pYUB8 which has no insertion element nor mycobacterial origin, but has an aph gene. A control of cells alone having no plasmid was also electroporated and plated in an identical fashion to the samples, to estimate the level of spontaneous resistance to kanamycin (or "background").

Within each experiment, the same amount of plasmid was transformed. In Experiment 1, 0.2 μg of plasmid was transformed. In Experiment 2, 5 μg of plasmid were transformed. In Experiments 3 through 5, 400 ng of plasmid were transformed, except that in Experiment 3, 1 μg of plasmid pYUB285 was transformed.

For the oriM control plasmid, from 0.2 μg to 0.4 μg of plasmid was used, and the numbers in Table 2 below are represented as transformants per μg. In Experiments 1 and 2, pYUB53 was used, and in Experiments 3 through 5, pMV261 was employed. In Experiments 1, and 3 through 5, transformants were recovered after electroporation at 30° C. In Experiment 2, transformants were recovered after electroporation at 37° C. In Table 2 below, dashes represent data not obtained. All results are given in Table 2 below.

TABLE 2

| | Plasmid | | | | | | |
|---|---|---|---|---|---|---|---|
| Experiment | pYUB285 | pYUB297 | pYUB305 | pYUB312 | pYUB8 | none | ori$^+$M/μg |
| 1 | 255 | — | — | — | 14 | — | $4.5 \times 10^4$ |
| 2 | 155 | 104 | — | — | 16 | 31 | $1.5 \times 10^4$ |
| 3 | 426 | 225 | — | 59 | — | 60 | $5 \times 10^4$ |
| 4 | 67 | 98 | 18 | 3 | — | 6 | $4.4 \times 10^4$ |
| 5 | 325 | — | 60 | 41 | — | 36 | $1.3 \times 10^5$ |

The results show that in each experiment a transformation frequency of $10^4$–$10^5$/μg with the oriM-containing plasmid is observed, and a number of kanamycin-resistant colonies arising from transformation with pYUB285 or pYUB297 are also obtained. These numbers are well above background from any of the controls and is suggestive of transposition. Furthermore, while pYUB285 contains Tn5367 having both ORFs of the IS element intact, pYUB297 carries Tn5368 in which ORFR is disrupted, implying that this ORF is not required for transposition. In addition, the numbers of colonies obtained for pYUB305, the construct carrying Tn5369, in which ORFA is disrupted, are sharply reduced to close to background levels, suggesting that this ORF is required for transposition and is likely to be the transposase. There is no evidence of illegitimate integration of plasmids since transformation with pYUB312 or pYUB8 yields numbers at background levels.

Analysis of Kanamycin-Resistant Colonies Using Southern Blotting.

Twenty colonies arising from transformation of pYUB285 and pYUB297 were picked at random from Experiment 2, grown up in the presence of kanamycin and examined by Southern blotting using three different enzymes and plasmid pYUB285 as probe. The Southern blot results of six of such clones, strains mc$^2$826–mc$^2$831, are shown in FIG. 32. Using KpnI, one fragment hybridizes in each clone (FIG. 32A) since there is no KpnI site in the transposon. To verify that insertion was random, BamHI was also used. This enzyme cuts once within the transposon, and when probed with plasmid, two bands are seen, corresponding to fragments obtained from the transposon's insertion into the chromosome (FIG. 32B). These fragments appear to be of random size, and indicate that mc$^2$830 and mc$^2$831, which yield similar-sized KpnI fragments, are not identical clones. Digestion with PvuI, and hybridization with plasmid was carried out in order determine whether any plasmid sequences were present; which might suggest the presence of cointegrate intermediates; or an illegitimate recombination event, previously described in *M. bovis* BCG and *M. tuberculosis* (Kalpana, et al., 1991). The results are shown in FIG. 32C. Digestion of the delivery plasmids with PvuI yields several fragments, including one internal to the transposon (See FIG. 31). If transposition had occurred by simple insertion rather than replication and cointegrate formation, the expected bands from the transposon-containing clones should include this internal fragment and two additional bands resulting from the insertion of the transposon into the chromosome. Three bands were seen with Tn5367 insertions $mc^2826$, $mc^2827$, $mc^2828$; each with the expected internal band as well as two unique bands of differing size. Results for the ($mc^2$ clones transformed with Tn5368 show that one of the clones ($mc^2829$) gives three bands, but the other two, ($mc^2830$ and $mc^2831$), display only one additional band along with the expected internal fragment, suggesting that deletions of the transposon may be occurring. The absence of extra bands, however excludes the possibility of plasmid integration.

Figure 33B:
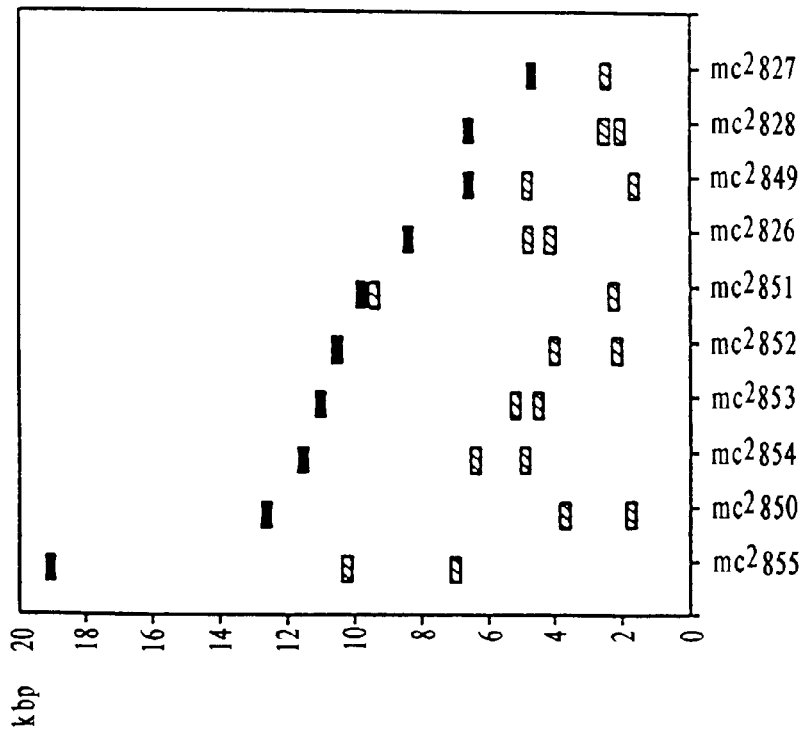
FIGS. 33A–33B. Graphic representation of Southern analysis showing apparent random nature of insertion of Tn5367 (FIG. 33A) and Tn5368 (FIG. 33B) into different restriction fragments in 19 clones. KpnI fragment sizes are plotted in descending order; BamHI fragments corresponding to each clone are superimposed.
Figure 33A:
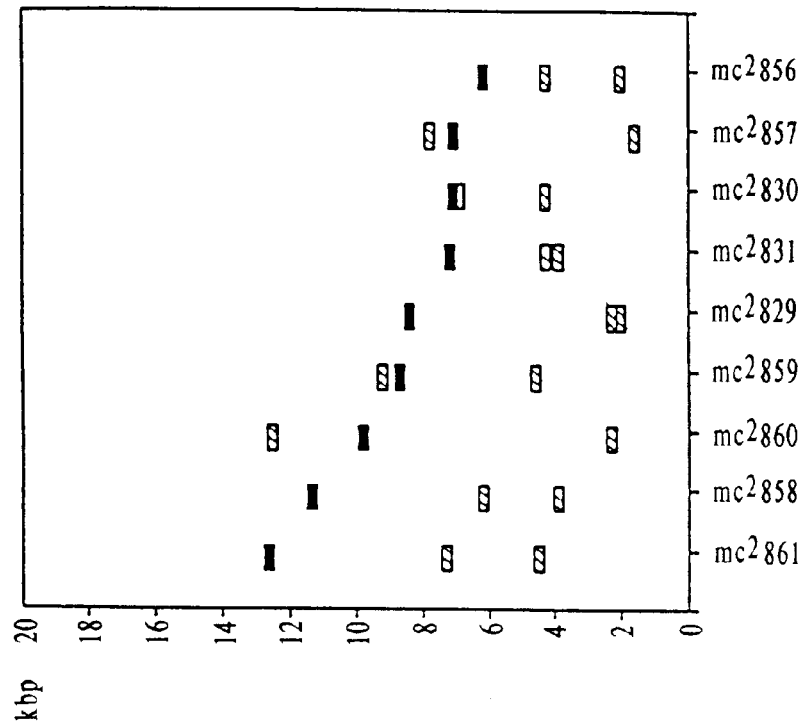

Of the 20 colonies analyzed in total, one clone did not hybridize on Southern blot, suggesting that its kanamycin resistance was due to a spontaneous mutation. The results of Southern blots of the remaining 19 clones with KpnI and BamHI have been analyzed and are represented graphically in FIG. 33, to illustrate the apparently random nature of insertion of Tn5367 and Tn5368 into different restriction fragments in each clone. The KpnI fragment sizes have been plotted in descending order and the BamHI fragments corresponding to each clone are superimposed. This representation of the data was chosen so that results for each enzyme could be combined, to show that the insertion site of the transposon differs for each clone. Even clones showing similar-sized KpnI fragments differ in the size of the BamHI fragment into which the transposon has inserted. No plasmid sequences were detected after Southern blotting using PvuI (results not shown).

Figure 34:
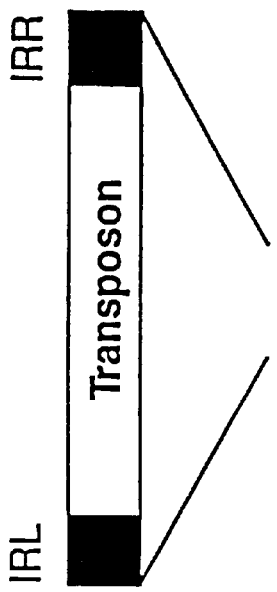
FIG. 34. Sequences of target sites of IS1096 insertion in clones mc²826—mc²831.

Sequencing of insertion junctions. IS1096 creates 8-base pair direct repeats on insertion into its target site; thus, sequencing was performed on the six clones ($mc^2826$–$mc^2831$) described above, to confirm that the transposons retained this property, and to investigate any target-site preference. The sequences of the duplicated target sites are given in FIG. 34. There is a weak consensus at the insertion junctions of XXXTA/TXC/GX, where T always stands at position 4, and it is noted also there is a preference in the target site for an AT-rich center and GC-rich ends. No similarities can be seen between clones comparing 50 base pairs of flanking DNA (data not shown).

Isolation and characterization of auxotrophic mutants. 923 kanamycin-resistant colonies resulting from the first and second experiments, were arrayed in 96-well plates, grown up, washed, and tested for auxotrophy by patching onto plates lacking amino acid supplement.

Promising candidates were tested in auxanography and three auxotrophs were found, one for methionine ($mc^2789$) and two for leucine ($mc^2797$ and $mc^2798$). The leucine mutants appear to be distinct as $mc^2798$ grows more slowly than $mc^2797$. The growth of all three auxotrophs could be supported in liquid or solid minimal media by the addition of the relevant amino acid.

Figure 35:
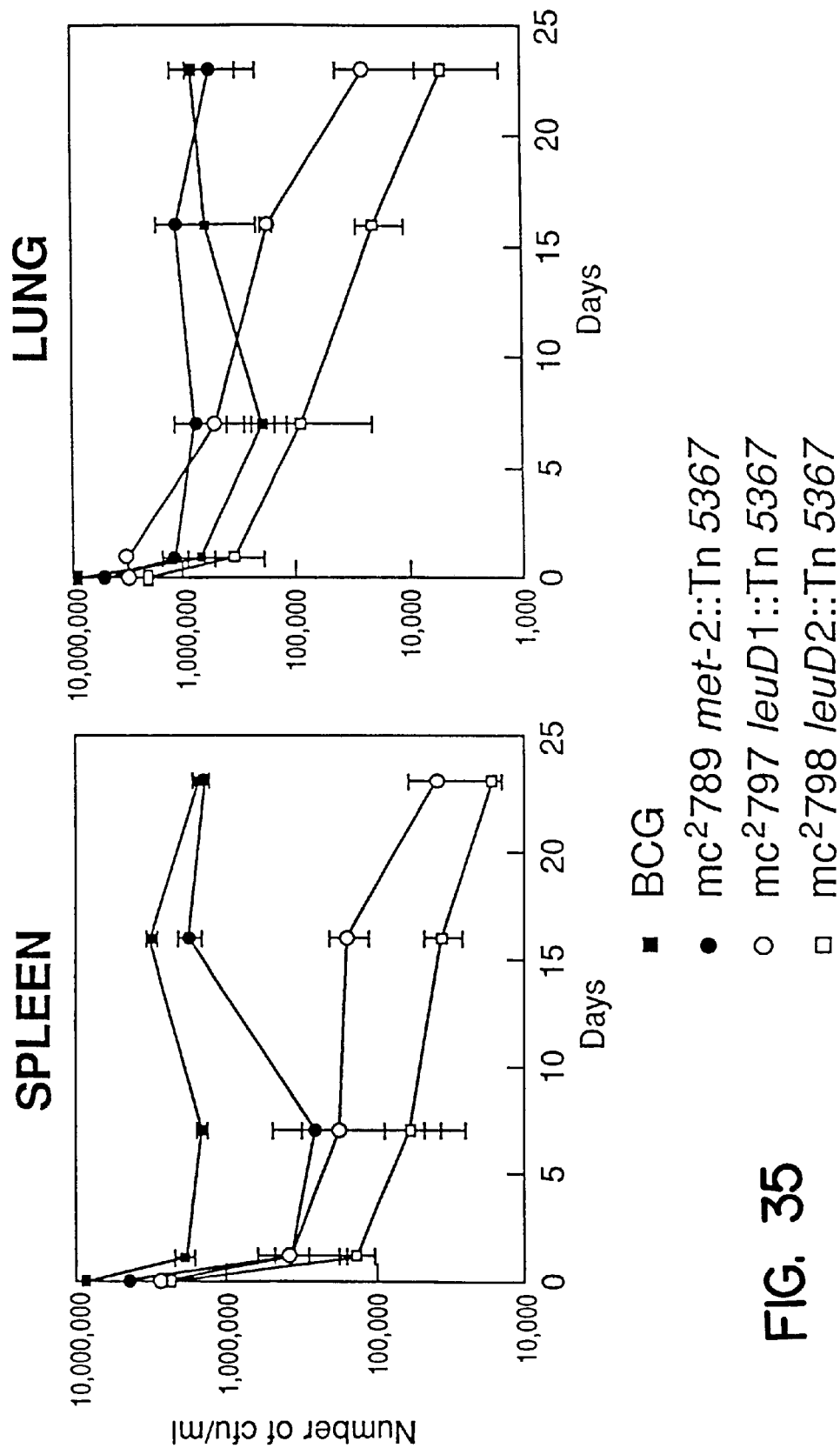
FIG. 35. Survival of BCG auxotrophs in mice.

The reversion frequencies for the auxotrophs $mc^2797$ (a leucine auxotroph containing Tn5367), $mc^2798$ (a leucine auxotroph containing Tn5366), and $mc^2789$ (a methionine auxotroph containing Tn5367) were between $10^{-7}$ and $10^{-8}$. The auxotrophs possess varying properties when grown in mice. As shown in FIG. 35, the methionine auxotroph resembles BCG when inoculated in the mouse. In contrast, both leucine auxotrophs are cleared rapidly from both mouse spleens and lungs.

DISCUSSION

A transposon capable of random insertional mutagenesis in the *M. tuberculosis* complex is an invaluable addition to the available tools for genetic manipulation of the Mycobacteria. Firstly, it allows the isolation of auxotrophic mutants of *M. bovis* BCG and *M. tuberculoisis*, which would be useful in new vaccine development, and in new approaches to the study of virulence such as in vivo expression technology (IVET) (Mahan, et al., *Science,* Vol. 259, pgs. 686–688 (1993)). It would also facilitate the analysis of mechanisms of invasion and survival in the host, and could lead to the identification of new drug targets in *M. tuberculosis.* Finally, the ability to mutate genes and locate them easily, is essential in the *M. tuberculosis* complex where gene replacement by homologous recombination is difficult (Kalpana, et al., 1991; Aldovini, et al., *J. Bacteriol.*, Vol. 175, pgs. 7282–7289 (1993)).

This example has shown that transposons derived from IS1096 do transpose in BCG and that while ORFA (tnpA) is required, ORFR (tnpR) is not. The products of transposition appear to be the insertion of one copy of the transposon, no cointegrates or plasmid sequences being detected.

It is concluded that if ORFR is indeed a resolvase, it is not required for transposition or resolution in *M. bovis* BCG. It is noted, however, that two of the clones analyzed by Southern blot using, PvuI showed evidence of deletions and both of these clones were derived from transformation with Tn5368, having an insertion in ORFR.

In nineteen out of twenty clones isolated at random, the transposons were found in different sites in the chromosome, as evidenced by restriction fragment size on Southern blotting. In each of the six insertions sequenced, a target duplication of eight base pairs was seen to either side of the element. The DNA sequence of the insertion site differed in each clone analyzed, with only a weak consensus, indicating that there is little constraint on insertion site. Two of the clones have the sequence ATAA at the center. The random nature of the transposition and the ability of the transposons to insert into coding regions is demonstrated by the isolation of methionine and leucine auxotrophs in BCG. No evidence for integration of the plasmid or illegitimate recombination, as originally described in the *M. tuberculosis* complex by Kalpana et. al., (1991), was seen in the nineteen clones examined.

It is not possible to estimate the transposition frequency in BCG from this example, only that transformation with the delivery plasmids yielded random insertional mutants at around $10^2$ per electroporation. This efficiency, however, was only obtained in five out of more than twenty experiments performed. The remaining transformations yielded kanamycin resistant colonies at a rate between zero and twice background numbers. This inconsistency between experiments could be explained by a link between transposition and the growth state of the culture, or other currently unknown regulations of the transposase promoter. Nonetheless, the efficiency was sufficient in the experiments reported here to obtain a library of useful insertional mutants. The high rate of transposition was probably due to the presence, on the delivery plasmid, of remnants of the mycobacterial origin left after the DraIII deletion. The sequence of the origin has been determined by two independent groups who assigned the ORFs differently (Rauzier, et al., 1988; Labidi, et al., 1992). The DraIII deletion eliminates sequence considered important by both groups and contains a region with nucleotide sequence homologies to the *E. coli* RK6 origin. Further studies must be initiated to elucidate the properties and stability of this disabled origin and to develop more efficient delivery systems for these transposons. It is also possible that changing the conditions for electroporation might increase transformation efficiency as described by Aldovini, et al., 1992, who found an increased number of transformants when using cultures maintained in log phase or treated with glycerine before electroporation. Other delivery systems which may be considered are the use of conjugation (Gormley, et al., *J. Bacteriol.*, Vol. 173, pgs. 6705–6708 (1991)); conditionally replicating phages with a deleted attachment site; mini-transposon derivatives with an inducible transposase; or a temperature-sensitive plasmid, such as that recently described for mycobacteria by Guilhot, et al., *FEMS Microbiology Letters*, Vol. 98, pgs. 181–186 (1992); or a combination of a plasmid and phage as has been described in Streptomyces (McHenney, et al., *J. Bacteriol.*, Vol. 173, pgs. 5578–5581 (1991)).

*M. bovis* BCG is a member of the *M. tuberculosis* complex; being derived from *M. bovis* which causes tuberculosis in humans. BCG and *M. tuberculosis* are closely related, so these transposons should function in *M. tuberculosis* and enable dissection of interesting genes; such as those involved in metabolism, drug resistance or genes responsible for pathogenesis.

It is to be understood, however, that the scope of the present invention is not to be limited to the specific embodiments described above. The invention may be practiced other than as particularly described and still be within the scope of the accompanying claims.

What is claimed is:

1. A recombinant mycobacterium comprising at least one mycobacterial gene containing an insertional mutation, wherein said mycobacterial gene is integrated into the mycobacterial genome and wherein the recombinant mycobacterium is auxotrophic for at least one of isoleucine, leucine, methionine, valine, or pyridoxine.

2. The mycobacterium of claim 1, wherein the insertional mutation is effected by homologous recombination.

3. The mycobacterium of claim 1, wherein the insertional mutation is effected by illegitimate recombination.

4. The recombinant mycobacterium of claim 1, wherein the recombinant mycobacterium is *M. tuberculosis*.

5. The recombinant mycobacterium of claim 1, wherein the recombinant mycobacterium is *M. bovis*-BCG.

6. The recombinant mycobacterium of claim 1, wherein the recombinant mycobacterium is *M. bovis*.

7. The mycobacterium of claim 1, wherein the insertional mutation is effected by a transposon.

8. The recombinant mycobacterium of claim 1, wherein the recombinant mycobacterium is auxotrophic for isoleucine.

9. The recombinant mycobacterium of claim 1, wherein the recombinant mycobacterium is auxotrophic for leucine.

10. The recombinant mycobacterium of claim 1, wherein the recombinant mycobacterium is auxotrophic for methionine.

11. The recombinant mycobacterium of claim 1, wherein the recombinant mycobacterium is auxotrophic for valine.

12. The recombinant mycobacterium of claim 1, wherein the recombinant mycobacterium is auxotrophic for pyridoxine.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 2275 base pairs
      (B) TYPE: nucleic acid
      (C) STRANDEDNESS: double
      (D) TOPOLOGY: linear (ii) MOLECULE TYPE: genomic DNA (vi) ORIGINAL SOURCE:
      (A) ORGANISM: M. smegmatis (ix) FEATURE:
      (A) NAME/KEY: transposon IS1096

(xi) SEQUENCE DESCRIPTION: SEQ ID NO: 1:

```
GGTTTTCTGG CTCTTCGCAC TTGACGGTGT AGAGACGATC AGCTGCTTTC GCGCTGTGAT      60

CGAGGGGTCT GGTTGGCTTG GGGTGTGCCG GAGAAGAAGC GGAAGAGCAA GAGGAAGAGC     120

GGAGTGTCCG GGGGCAGTGT GGACCTGGCG TTGCTGCAGA AGCTAATGGC CGACGCTGGT     180

CGGAACGTGT TCGCGGGAAT GTTCGATGAG CCGACGCCCG AGGTGCGGGC GGTGCCGGAT     240

CGTGCGCGGG GCTTCCGGGT GCGCGTCGAC CTGATGTACG CCAAGCCGCC GATCTGGCGT     300

CGGCTGGACC TGCCGGGCGA CCTCATGCTC GATGAGCTCC ATGTTGTGCT GCAGGTCGTT     360

ATGGGCTGGC AGGACAGTCA TCTGCATAAG TTCGGTGTCG GGGCGGACCG GCGGACCCGT     420

GCCTACTTCG TCACCGGGTT TGATCTCAGC GAAGGCGACG ACGGTGTCGT CGAGGACAGC     480

GTGCGCCTCG ATCAGGTGGT GTCCGATAAG GGCGAGCGGT TGTTCTACGA TTACGACTTC     540

GGCGACGGAT GGGACCACGT GCTCGTGGTC GAAGACGTTT TCGATGATCC GCCCCCGGCT     600

GCGGTGTGTC TGACGGGAAA GATGGCCTGT CCGCCGGAGG ACTGTGGTGG CCTGGGCGGC     660

TATGAGGAGT TGGCTGCGTG GGTTCGCGGC GGGTACGACC CGCGGGAAAC GCCGATGGGA     720

CTCGGTGCGC AGGAGATGAG GGACTGGCTG CCCCCGGGGC TGGCACCCCG ACCGTTTCTC     780

GGTGGCCGAG ACCAATGACG CTCTGGCCGC GTTGAACACG CGTTGAGGAT TCTTCACCGC     840

CGAGGTTGAC GGAGCTGGGT TCGGAAGCCT CCGGTCTCGA GCAGGGACCG GGCGATGTAG     900

TTGGTGAGGT TGCGGAAGCC CAGGGCGGAT CCGCGCAGGT GTTCGAGGCC GCCGTTGATC     960

GCTTCGGTCG GCCCGTTGGA GGTGCCGGGG CGGTCGAAGT AGGCCAGGAC GTCGGCGGCA    1020

CGCTTCTTCA GTGTCCGCCC GAGGGTGATC AGCTCGGTCA GCGACGTGGG GACGCCTGTG    1080

CTCAGCGTGG TGATCAGTGC AGCCATCATG GTGCGGCCCT TGGTGCGGTC TGGTTCGCGG    1140
```

-continued

| | |
|---|---|
| TAGGCGGCCA CGGTGCGTTG ATACATCGCC CAGGTGGCCT CGATCTCGGC GTGCCCGTTG | 1200 |
| GCGGCGAACA GTGCGGCCAG TCGGGCTTTC TGGCGGTCGC TGAGCAGGTC GGCCCCGGTG | 1260 |
| TGCAGGGTGC TGCGCGATCG GTAGAGCGGG TCGGTGCTGC GGCCGCGGTG CCCGCAGGTG | 1320 |
| GCCAGCTGCA CGCGGCGTCG GCACTCGTCG AGGGCGTTGC CGGCCAGGCG GACCACGTGG | 1380 |
| AAGGGGTCCA TCACCGTGGC CGCGTCAGGC AGTTCTTCGG TGGCGGCGGT CTTGAACCCG | 1440 |
| GAGAACCCGT CCATGGCAAC AACGTCCACA CGATCACGCC ACTCCTGTGG CCGCTGTGCC | 1500 |
| AGCCAGTCGG CGAACGCCTT CTTGGAGCGG CCCTCCACCA TGTCGAGCAG CCGTGCGGGG | 1560 |
| CCGGTCCCGT CACGCACGGG CGTGAGATCG ATGATGACGG TGACGTACTT GTCGCCGCGC | 1620 |
| CGAGTGTGCC GCCACACGTG CTCATCGACG CCGATCACCG CGACGCCATC GAACCGGGCC | 1680 |
| GGATCGGCGA TGAGCACCCG CTGACCTTCG GCGAGCACGG CGTTGTTGGC AGTGTTCCAC | 1740 |
| GACACCGCAA GCGCCTCGGC GACCCGGGCC ACCGACAGGT GTTGGCAGAC AAGGGCTTCC | 1800 |
| AGCGCCCACC GCAGAGCACG CCGGGACAGC CTGGCCCGCG GTTCGGCTGC GGGGCTGGCA | 1860 |
| TCCTGGCGCC ACACATGAGC GCAGCCGGCG CAACGGTAAC GGCGGATCGT GACCAGCAAA | 1920 |
| GCCGTGGGTC GCCACCCGAA CGGTTCATGA GCCAACGTGC GAGTCACGCT GTCACGTACA | 1980 |
| ACGCCTTCTT CGCCGCAGCG GCGGCACCAC CGATCCTCAT CGGCGACCCG GCACGCCAGC | 2040 |
| ACGGCCCGAT CAGGGTCGAG GCGTTGGCCG GTCACCTCCA ACCCGAGCTC GTCGAGGCGG | 2100 |
| CAGAAAGTGG TCAGGTCAGC GCAGGCGAAG CCCGCACCGA CCGGTAGCGT CAGGCACGTC | 2160 |
| GAGGTGTTTC AGATGGATGG CGTAGGAACC TCCATCATCG GAAGACCTCG ACCCCTATCC | 2220 |
| CGGCACCGAC GCGCCGACGA CCTCTACACC CTCAACTGCG AAGAGCCGGT TTTCT | 2275 |